United States Patent [19]

Bovy et al.

[11] Patent Number: 5,441,974
[45] Date of Patent: Aug. 15, 1995

[54] PHENYL AMIDINES LACTONES USEFUL AS PLATELET AGGREGATION INHIBITORS

[75] Inventors: Philippe R. Bovy, Los Altos, Calif.; Thomas E. Rogers, Ballwin, Mo.; Masateru Miyano, Salem, S.C.; Joseph G. Rico, Manchester, Mo.

[73] Assignee: G. D. Searle & Co., Chicago, Ill.

[21] Appl. No.: 244,421

[22] PCT Filed: Dec. 11, 1992

[86] PCT No.: PCT/US92/10526

§ 371 Date: May 25, 1994

§ 102(e) Date: May 25, 1994

[87] PCT Pub. No.: WO93/12103

PCT Pub. Date: Jun. 24, 1993

[51] Int. Cl.$^6$ .............. A61K 31/425; C07D 311/012
[52] U.S. Cl. .................... 514/365; 514/456; 514/471; 548/204; 549/285; 549/289; 549/290; 549/295; 549/313
[58] Field of Search ............ 549/285, 289, 290, 295, 549/313; 548/204; 514/365, 456, 471

[56] References Cited

U.S. PATENT DOCUMENTS

| | | | |
|---|---|---|---|
| 4,517,686 | 5/1985 | Ruoslahti et al. | 3/1 |
| 4,578,079 | 3/1988 | Ruoslahti et al. | 623/11 |
| 4,589,881 | 5/1986 | Pierschbacher et al. | 623/11 |
| 4,614,517 | 9/1986 | Ruoslahti et al. | 623/11 |
| 4,661,111 | 4/1987 | Ruoslahti et al. | 623/11 |
| 4,683,291 | 7/1987 | Zimmerman et al. | 530/324 |
| 4,791,102 | 12/1988 | Bernat et al. | 514/19 |
| 4,857,508 | 8/1989 | Adams et al. | 514/18 |
| 4,879,313 | 11/1989 | Tjoeng et al. | 514/616 |
| 4,977,168 | 12/1990 | Bernat et al. | 514/330 |

FOREIGN PATENT DOCUMENTS

| | | | |
|---|---|---|---|
| 0275748 | 7/1988 | European Pat. Off. | C07K 7/06 |
| 0298820 | 1/1989 | European Pat. Off. | C07K 7/06 |
| 0372486 | 6/1990 | European Pat. Off. | C07C 27/14 |
| 0381033 | 8/1990 | European Pat. Off. | C07C 31/19 |
| 0410540 | 1/1991 | European Pat. Off. | C07K 7/06 |
| 445796 | 9/1991 | European Pat. Off. | C07K 5/06 |

OTHER PUBLICATIONS

M. Kloczewiak et al. Platelet Receptor Recognition Site onb Human, etc. Biochemistry 23 (8), 1767–1774–(-Jan. 1984).

Z. Ruggeri et al. Inhibition of Platelet Function with Synthetic, etc. Proc. Nat'l Acad. Sci., USA 83, 5708–5712 (Aug. 1986).

E. Plow et al. The Effect of ARG-GLY-ASP-Containing Peptides, etc. Proc. Nat'l Acad. Sci., USA 82, 8057–8061 (Dec. 1985).

M. Ginsberg et al. Inhibition of Fibronectin Binding to Platelets, etc. The Journal of Biological Chemistry, 260(7), 3931–3936 (Apr. 1985).

D. Haverstick et al. Inhibition of Platelet Adhesion to, etc. Blood 66(4) 946–952 (Oct. 1985).

E. Ruoslahti et al. New Perspectives in Cell Adhesion: RGD and, etc. Science, 23 491–497 (Oct. 1987).

R. Gould et al. Disintegrins: A Family of Integrin Inhibitory, etc. Proc. Soc. Exp. Biol. and Med. 195(2), 168–171 (Nov. 1990).

R. Ferroni et al. "Ethyl Esters of N-amidinobenzoyl Amino Acids: Inhibitory Effects on Thrombin, Blood Coagulation and Platelet Aggregation" Chemical Abstracts, vol. 108, No. 7, 15 Feb. 1988, Columbus, Oh. US; Abstract No. 48724q.

*Primary Examiner*—C. Warren Ivy
*Assistant Examiner*—A. A. Owens
*Attorney, Agent, or Firm*—Joy Ann Serauskas; Roger A. Williams

[57] ABSTRACT

This invention relates to compounds having the following formula

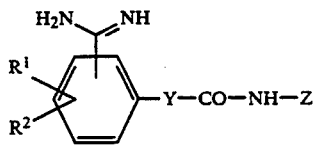

wherein Z is a lactone or a lactone which is fused to a benzene ring which are useful in the inhibition of platelet aggregation. This invention also relates to pharmaceutical compositions of such phenyl amidines derivatives.

12 Claims, No Drawings

PHENYL AMIDINES LACTONES USEFUL AS PLATELET AGGREGATION INHIBITORS

FIELD OF THE INVENTION

This appliation is a 371 of PCT/US92/10526 filed Dec. 11, 1992.

This invention is in the field of mammalian therapeutics and relates to compounds for the treatment of mammalian disorders such as cardiovascular disorders. Of particular interest is a class of phenyl amidines derivatives useful as inhibitors of platelet aggregation.

Background of the Invention

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gp IIb-/IIIa; this is an important feature of the platelet function. Inhibitors of this interaction are useful in modulating platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. See U.S. Pat. Nos. 4,517,686; 4,589,881; and 4,661,111. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517.

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., *Biochem.* 23, 1767–1774 (1984); Plow et al., *Proc. Natl. Acad. Sci.* 82, 8057–8061 (1985); Ruggeri et al., *Ibid.* 83, 5708–5712 (1986); Ginsberg et al., *J. Biol. Chem.* 260 (7), 3931–3936 (1985); Hayerstick et al., *Blood* 66 (4), 946–952 (1985); and Ruoslahti and Pierschbacher, *Science* 238, 491–497 (1987). Still other such inhibitory peptides are disclosed in EP Patent Applications 275,748 and 298,820.

U.S. Pat. No. 4,879,313 discloses compounds useful as inhibitors of platelet aggregation having the formula:

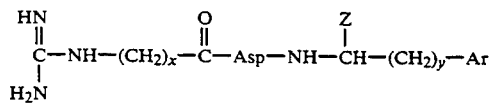

wherein
x = 6 to 10,
y = 0 to 4,
Z = H, COOH, CONH$_2$ OR C$_{1-6}$ alkyl,
Ar = phenyl, biphenyl or naphthyl, each substituted with 1 to 3 methoxy groups, or an unsubstituted phenyl, biphenyl, naphthyl, pyridyl or thienyl group, and
Asp = aspartic acid residue.

U.S. Pat. No. 4,977,168 discloses compounds having the following structural formula:

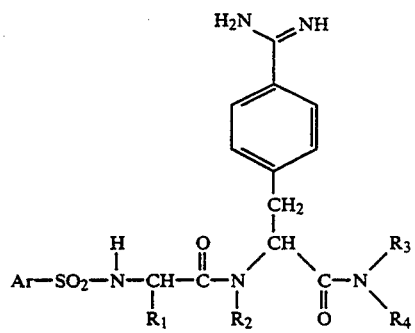

wherein

R$_1$ represents hydrogen, a lower alkyl group, a lower hydroxyalkyl group, a benzyl group, a phenyl group or a 4-hydroxyphenyl group;

R$_2$ represents a lower alkyl, lower alkenyl, lower alkynyl or benzyl group, or a lower alkoxycarbonylalkyl, lower carboxyalkyl, or lower hydroxyalkyl group;

R$_3$ and R$_4$, identical or different, each represents a lower alkyl or lower hydroxyalkyl radical, lower alkenyl or lower alkynyl radical or form together with the nitrogen to which they are attached, a saturated heterocycle such as morpholino, thiomorpholino, pyrrolidino not substituted or substituted by an alkoxycarbonyl or carboxy group, piperazino, 4-(lower alkyl)piperazino, 4-(lower hydroxyalkyl)-piperazino, or piperidino not substituted or substituted by one of the following groups: lower alkyl, benzyl, hydroxy, lower hydroxyalkyl, amino, lower aminoalkyl, hydroxyamino, alkoxycarbonyl or carboxy.

Ar represents a phenyl, alpha-naphthyl or beta-naphthyl group, possibly substituted, or a heteroaryl group chosen from the radicals pyridyl, quinolinyl, or isoquinolinyl, possibly substituted, as well as their isomers and their mixtures and their salts with pharmaceutically acceptable mineral or organic acids which are useful as antithrombotic agents. These compounds are structurally distinct from the present invention because they lack the lactone moiety of the present invention.

U.S. Pat. No. 4,791,102 discloses compounds having the following structural formula

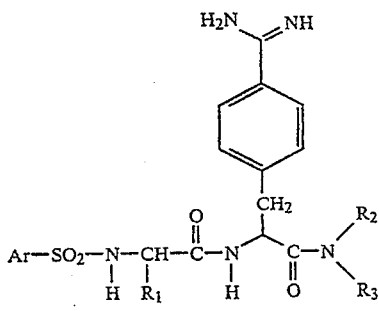

wherein

R₁ represents a lower alkyl, lower hydroxyalkyl, or benzyl group, a phenyl or a 4-hydroxyphenyl group.

R₂ and R₃, identical or different, each represents a lower alkyl or hydroxyalkyl, lower alkenyl or lower alkynyl radical, or they form together with the nitrogen to which they are attached, a saturated heterocycle such as morpholino, thiomorpholino, pyrrolidino unsubstituted or substituted by an alkoxycarbonyl or carboxyl group, piperazino, 4-(lower alkyl)-piperazino or piperidino unsubstituted or substituted by a lower alkyl, benzyl, hydroxy, lower hydroxyalkyl, amino, lower aminoalkyl, alkoxycarbonyl or carboxyl group.

Ar represents a phenyl, a possibly substituted alpha-naphthyl or beta-naphthyl group, or else a heteroaryl group chosen from pyridyl, quinolinyl, isoquinolinyl, possibly substituted which are useful as selective inhibiting agents of thrombin and antithrombotics. These compounds are structurally distinct from the present invention because they lack the lactone moiety of the present invention.

European Patent Application 372,486 discloses N-acyl beta amino acid derivatives of the formula:

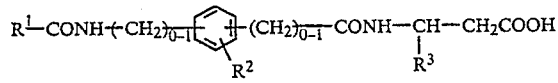

and their salts. Said compounds are useful for inhibiting platelet aggregation in the treatment of thrombosis, stroke, myocardial infarction, inflammation and arteriosclerosis, and for inhibiting metastasis.

European Patent Application 381,033 A1 discloses amidino or guanidino-aryl substituted alkanoic acid derivatives which are useful for the treatment of thrombosis, apoplexy, cardiac infarction, inflammation, arteriosclerosis and tumors. These compounds are structurally distinct from the present invention because they are aryl acetic acid/esters 2-amidino/guanidino substituted phenyl alkyl carbonyl amino derivatives in contrast to the compounds of the present invention which are lactones.

European Patent Application 445,796 A2 discloses acetic acid derivatives having the formula

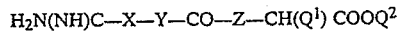

where

Q¹ stands for hydrogen, methyl or phenyl,

Q² stands for hydrogen, phenyl-low-alkyl or low alkyl that can be cleaved under physiological conditions, X stands for 1,4-phenylene, 2,5- or 3,6-pyridylene or, 1,4-piperidinylene, which is bonded to group Y through the C atom in the 4-position, Y is a group having the formula

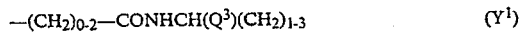

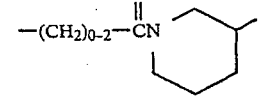

OR

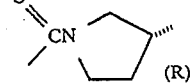

where

Q³ stands for hydrogen, methyl, phenyl, —COOH, —COO— low-alkyl, —CONH(CH₂)₂—COOH or —CONH(CH₂)₂—COO—low-alkyl, Q⁴ hydrogen, methyl or phenyl, Z a 1,4-piperazinylene group, a 1,4-piperazinylene group which is bonded to the CO group through the N atom in the 1-position or a group having the formula

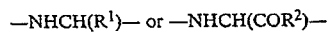

where

R¹ stands for hydrogen, methyl, phenyl or a —COO—low-alkyl,

R² stands for the residue of an α-aminocarboxylic acid bonded through the amino group or of an ester or amide thereof, or a group having the formula —NHCH₂CH₂—Ar, or —CO—R², if applicable, a mono- or di-low-alkylated carbamoyl group or a pyrrolidinoyl or piperidinoyl group, Ar stands for a phenyl or a phenyl substituted by low alkyl, low alkoxy, —COOH, —COO—low-alkyl, —O(CH₂)₁₋₄—COOH, —O(CH₂)₁₋₄—COO—low-alkyl, —CONH₂, —CONH—low-alkyl, —CON(low alkyl)₂, pyrrolidinoyl or piperidinoyl which are said to have inhibitory action on the bonding of adhesive proteins to blood platelets as well as blood platelet aggregation and cell-cell adhesion. These compounds are structurally distinct from the present invention because they are acetic acid/ester derivatives in contrast to the compounds of the present invention which are lactones.

Gould et al., Proc. Soc. Exp. Biol. Med., 195(2), November 1990, p. 168–171, discloses a new class of low molecular weight, RGD-containing crysteine-rich peptides. These peptides interact with the β₁ and β₃ families of integrins and their potency is at least 500–2000 times higher than short RGDX peptides.

Summary of the Invention

The present invention relates to a class of compounds represented by the formula:

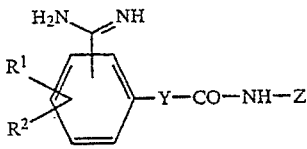

or a pharmaceutically acceptable salt thereof, wherein $R^1$ and $R^2$ are independently selected from the group consisting of hydrido, halo, alkoxy having 1 to 6 carbon atoms, alkyl having 1 to 6 carbon atoms and hydroxy;

Y is alkyl having 1 to 6 carbon atoms, alkenyl having 2 to 6 carbon atoms, alkynyl having 2 to 6 carbon atoms wherein each carbon atom of the above defined groups which is capable of further substitution may be further substituted by alkyl having 1 to 6 carbon atoms, phenyl or substituted phenyl wherein each phenyl substituent is selected from halo, alkoxy having 1 to 6 carbon atoms, and alkyl having 1 to 6 carbon atoms or Y is carbonylalkyl wherein the alkyl has 1 to 3 carbon atoms;

Z is a lactone which is represented by the formula

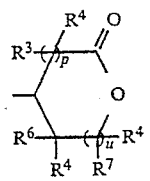

wherein $R^3$ and $R^4$ are each independently selected from the group consisting of hydrido, halo, alkoxy having 1 to 6 carbon atoms, alkyl having 1 to 6 carbon atoms and hydroxy;

$R^5$, $R^6$, $R^7$ and $R^8$ are each independently selected from the group consisting of hydrido; halo; alkenyl having 2 to 6 carbon atoms; alkynyl having 2 to 6 carbon atoms; alkoxy having 1 to 6 carbon atoms; alkyl having 1 to 6 carbon atoms; phenyl; substituted phenyl wherein each phenyl substituent is selected from halo, alkoxy having 1 to 6 carbon atoms and alkyl having 1 to 6 carbon atoms and heteroaromatic ring having 5 or 6 ring carbon atoms wherein one or two of the carbon atoms are replaced by a heteroatom selected from nitrogen, oxygen or sulfur with the understanding that if two hetero atoms are present one of the hetero atoms must be nitrogen;

p is an integer from 1 to 2;

u is an integer from 0 to 2;

or

Z is a lactone which is fused to a benzene ring and represented by the formula

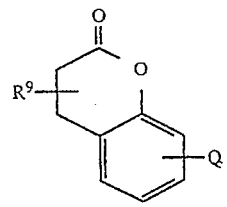

wherein

Q is one or more substituents of the benzene ring which may be in any position and is selected from the group consisting of hydrido, halo, hydroxy, alkyl having 1 to 6 carbon atoms and alkoxy having 1 to 6 carbon atoms and $R^9$ is hydrido, alkyl having 1 to 6 carbon atoms or alkoxy having 1 to 6 carbon atoms.

The invention further relates to pharmaceutical compositions comprising a compound of Formula I. Such compounds and compositions have usefulness as inhibitors of platelet aggregation. The invention also relates to a method of inhibiting platelet aggregation in a mammal in need of such treatment.

A preferred embodiment of the present invention is a compound of the formula

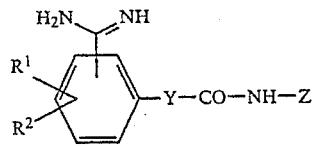

or a pharmaceutically acceptable salt thereof, wherein $R^1$ and $R^2$ are independently selected from the group consisting of hydrido, halo, alkoxy having 1 to 6 carbon atoms, alkyl having 1 to 6 carbon atoms and hydroxy;

Y is alkyl having 1 to 6 carbon atoms, alkenyl having 2 to 4 carbon atoms, alkynyl having 2 to 4 carbon atoms or carbonylalkyl wherein the alkyl has 1 to 3 carbon atoms;

Z is a lactone which is represented by the formula

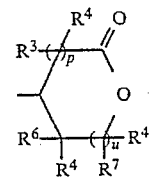

wherein $R^3$ and $R^4$ are independently selected from the group consisting of hydrido, halo, alkoxy having 1 to 6 carbon atoms, alkyl having 1 to 6 carbon atoms;

$R^5$, $R^6$, $R^7$ and $R^8$ are each independently selected from the group consisting of hydrido; alkoxy having 1 to 6 carbon atoms; alkyl having 1 to 6 carbon atoms; phenyl; substituted phenyl wherein each phenyl substituent is selected from halo, alkoxy having 1 to 6 carbon atoms and alkyl having 1 to 6 carbon atoms and heteroaromatic ring having 5 or 6 ring carbon atoms wherein one or two of the carbon atoms are replaced by a heteroatom selected from nitrogen, oxygen or sulfur with the understanding that if two hetero atoms are present one of the hetero atoms must be nitrogen;

p is an integer from 1 to 2;

u is an integer from 0 to 2;

or

Z is a lactone which is fused to a benzene ring and represented by the formula

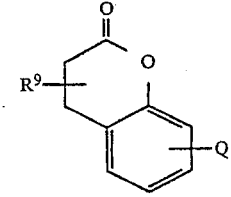

wherein

Q is one or more substituents of the benzene ring which may be in any position and is selected from the group consisting of hydrido, halo, hydroxy, alkyl having 1 to 6 carbon atoms and alkoxy having 1 to 6 carbon atoms and $R^9$ is hydrido.

A further preferred embodiment of the present invention is a compound of the formula

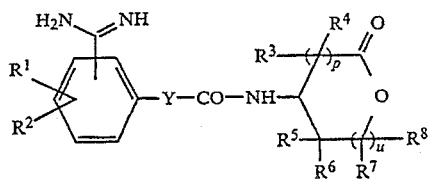

or a pharmaceutically acceptable salt, thereof wherein $R^1$ and $R^2$ are independently hydrido;

Y is alkyl having 1 to 6 carbon atoms;

$R^3$ and $R^4$ are independently selected from the group consisting of hydrido, halo, alkoxy having 1 to 6 carbon atoms, alkyl having 1 to 6 carbon atoms and hydroxy;

$R^5$, $R^6$, $R^7$ and $R^8$ are each independently selected from the group consisting of hydrido; alkoxy having 1 to 6 carbon atoms; alkyl having 1 to 6 carbon atoms; phenyl; substituted phenyl wherein each phenyl substituent is selected from halo, alkoxy having 1 to 6 carbon atoms and alkyl having 1 to 6 carbon atoms and heteroaromatic ring having 5 or 6 ring carbon atoms wherein one or two of the carbon atoms are replaced by a heteroatom selected from nitrogen, oxygen or sulfur with the understanding that if two hetero atoms are present one of the hetero atoms must be nitrogen;

p is an integer from 1 to 2 and u is an integer from 0 to 2.

Exemplifying this embodiment are the following compounds:

4-[aminoiminomethyl]-N-[5-oxo-3S-furanyl]benzenepentanamide;

4-(aminoiminomethyl)-N-[2-(thiazol-2-yl)-5-oxo-3S-furanyl]pentanamide;

4-(aminoiminomethyl)-N-(tetrahydro-5-oxo-2-(2-thiazolyl)-3S-furanyl)benzenepentanamide, bis(trifluoroacetate) (diastereoisomer A); and 4-(aminoiminomethyl)-N-(tetrahydro-5-oxo-2-phenyl-3S-furanyl)benzenepentanamide, trifluoroacetate (diastereoisomer B).

Another preferred embodiment of the present invention is a compound of the formula

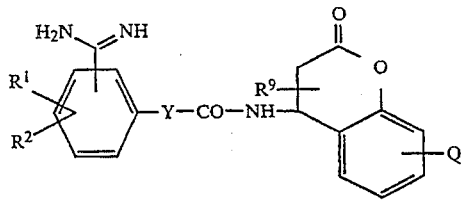

or a pharmaceutically acceptable salt thereof, wherein $R^1$ and $R^2$ are independently hydrido;

Y is alkyl having 1 to 6 carbon atoms; and

Q is one or more substituents of the benzene ring which may be in any position and is selected from the group consisting of hydrido, halo, hydroxy, alkyl having 1 to 6 carbon atoms and alkoxy having 1 to 6 carbon atoms and $R^9$ is hydrido.

Exemplifying this embodiment are the following compounds:

(±)-4-(aminoiminomethyl)-N-(3,4-dihydro-7-methoxy-2-oxo-2H-1-benzopyran-4-yl)benzenepentanamide and (±)-4-(aminoiminomethyl)-N-(3,4-dihydro-2-oxo-2H-1-benzopyran-4-yl)benenepentanamide.

As used herein, the term "hydrido" denotes a single hydrogen atom (H). This hydrido group may be attached, for example, to a oxygen atom to form a hydroxyl group; or, as another example, two hydrido groups may be attached to a carbon atom to form a —CH$_2$— group.

As used herein, the term "alkyl" embraces a linear or branched chain saturated hydrocarbon radical having 1 to 6 carbon atoms. Illustrative of such radicals are methyl, ethyl, propyl, 1-methylethyl, butyl, 2-methylpropyl, 1-methylpropyl, 1,1-dimethylethyl, pentyl, 3-methylbutyl, 1-methylbutyl, 1-ethylpropyl, 2,2-dimethylpropyl, 1,1-dimethylpropyl, hexyl, and 4-methylpentyl.

As used herein, the term "alkoxy" embraces linear or branched oxy-containing radicals each having alkyl portions of 1 to 6 carbon atoms. Illustrative of such groups are methoxy, ethoxy, propoxy, butoxy, 1-methylethoxy, 2-methylpropoxy, 1-methylpropoxy, 1,1-dimethylethoxy, pentenoxy, 3-methylbutoxy, 1-methylbutoxy, 1-ethylpropoxy, 2-2-dimethylpropoxy, 1,1-dimethylpropoxy, hexoxy, and 4-methylpentoxy.

As used herein the term "alkenyl" embraces linear or branched unsaturated hydrocarbon radicals having 2 to 6 carbon atoms and containing at least one carbon to carbon double bond, which carbon to carbon double bond may have either cis or trans geometry within the alkenyl moiety. Illustrative of such groups are ethenyl, propenyl, butenyl, isobutenyl, pentenyl, 3-methyl-1-butenyl, 2-methyl-2-butenyl, 2,3-dimethyl-2-butenyl, and hexenyl.

As used herein the term "alkynyl" embraces linear or branched unsaturated hydrocarbon radicals having 2 to 6 carbon atoms and containing one carbon to Carbon triple bond. Illustrative of such radicals are ethynyl, propynyl, butynyl, isobutynyl, pentynyl, 2-methyl-2-butynyl, and hexynyl.

As used herein the term "halo" embraces halogen atoms. Illustrative of such atoms are chloro (Cl), fluoro (F), bromo (Br) and iodo (I).

As used herein the term "carbonylalkyl" represents the radical of the formula

COR wherein the R represents an alkyl group. Illustrative of such radicals are carbonylmethyl, carbonylethyl, carbonylpropyl, carbonylbutyl, carbonylpentyl and carbonylhexyl.

As used herein the term "heteroaromatic" embraces an unsaturated cyclic hydrocarbons structure having 5 or 6 ring carbon atoms wherein 1 or 2 of the ring carbon atoms are replaced by nitrogen, oxygen or sulfur. Illustrative of such heterocyclic hydrocarbon structures are pyridyl, furyl, pyranyl, pyrimidinyl, thienyl, pyrazinyl, pyridazinyl, imidazolyl, pyrazolyl, oxazolyl, thiazolyl and thiophenyl.

As used herein the term "carbon atom of the above defined groups which is capable of further substitution" refers to a carbon atom wherein one or more of its hydrogen atoms may be replaced by one or more substituents which are selected from the group consisting of alkyl having 1 to 6 carbon atoms, phenyl and substituted phenyl wherein each phenyl substituent is selected from hydrido, alkoxy having 1 to 6 carbon atoms and alkyl having 1 to 6 carbon atoms.

As used herein the term "lactone which is fused to a benzene ring" refers to a pyran-2-one ring which is fused to a benzene ring. This structure is represented by the following formula:

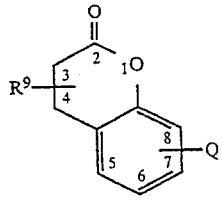

When Z of Formula I is substituted or unsubstituted benzopyran-2-one the point of attachment of the benzopyran-2-one portion to the remaining portion of the molecule represented by formula I is at the 3rd or 4th carbon of the benzopyran-2-one ring.

The compounds as shown in Formula I can exist in various isomeric forms and all such isomeric forms are meant to be included. Tautomeric forms are also included as well as pharmaceutically acceptable salts of such isomers and tautomers.

In the structures and formulas herein, the bond drawn across a bond of an aromatic ring can be to any available atom on the aromatic ring.

The term "pharmaceutically acceptable salt" refers to a salt prepared by contacting a compound of formula (I) with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, and tartrate salts. All of these salts may be prepared by conventional means by. reacting, for example, the appropriate acid with the corresponding compound of Formula I.

DETAILED DESCRIPTION OF THE INVENTION

The compounds of Formula I may be prepared by standard synthetic methods combined with methods analogous to solution phase peptide synthesis [see: The Peptides: Analysis, Synthesis, Biology (E. Gross and J. Meienhofer, eds.), Vol. 1-5, Academic Press, New York)].

General synthetic sequences are outlined in the following Schemes.

In Scheme 1 is described a general synthesis of the 5-(cyanophenyl)-pentanoic, -pentenoic and -pentynoic derivatives, substituted or not. A halobenzonitrile is coupled to an omega alkenoic or alkynoic acid using a palladium based coupling reaction ["Heck Reaction" -Palladium Reagents in Organic Syntheses (Richard F. Heck), Academic Press, New York, 1985; Heck, R. F. J. Amer. Chem. Soc., 1979, 12, 146-51. Tuyet, J. J. Chem. Soc., Chem. Commun. 1984, 1287-9]. The preferred conditions for the palladium coupling reaction generally differ for the alkynoic acid and the alkenoic acid coupling components. The preferred conditions for the alkynoic acid coupling component utilizes tetrakis(triphenylphosphine)-palladium as catalyst and piperidine as the solvent (for related conditions see: H. A. Dieck and F. R. Heck J. Organometallic Chem. 259–263 (1975)). Suitable conditions for the alkenoic acid coupling component utilize the phase transfer conditions of Jeffery and Larock [T. Jeffery J. Chem. Soc. Chem. Commun. 1287-89 (1984); R. C. Larock Tetrahedron Lett. 2603–2606 (1989)]. These extremely mild conditions (phase transfer agent-tetrabutylammonium salt, catalyst palladium (II) acetate, base-potassium acetate or triethylamine, dimethyl formamide) afford a good yield of coupled olefin. Compounds of Formula I where Y is a saturated chain (alkane) are obtained through a selective reduction of the double bond (Y is CH=CH) by catalytic reduction over palladium on calcium carbonate. The required omega alkenoic acids are commercially available or can be synthesized by oxidation of the omega alkenols [E. J. Corey and G. Schmidt Tetrahedron Lett. 399 (1979)]. The required omega alkynoic acids are commercially available or can be synthesized from omega haloalkanoic acids and lithium acetylide [W. J. DeJarlais, E. A. Emken Synth. Commun. 653 (1980); J. Cossy, J. P. Pete Tetrahedron Lett. 573 (1986)].

In Scheme 2 is described an alternative method for the preparation of the (cyanophenyl)alkenoic acid unit using a standard Wittig Reaction [B. E. Maryanoff, A. Reitz Chem Rev. 863–927 (1989)] with cyanobenzaldehyde and an omega substituted (carboxyalkyl)triphenylphosphonium bromide as the two reaction components [for related conditions see: J. Am. Chem. Soc,, 397 (1970); Ibid 6831 and 7185 (1973)].

In Scheme 3 are included examples of procedures to access compounds of Formula I where $R_1$ and $R_2$ are different from hydrogen. The substituents $R_1$ and $R_2$, (where $R_1$ and $R_2$ are each independently halo, alkyl, hydroxy, or alkoxy) can be present in the starting commercially available bromobenzonitrile (Scheme 1) cyanobenzaldehyde (Scheme 2) or introduced at a latter stage as indicated in Scheme 3. The ring can be halogenated using bromine, iodine, or chlorine (Scheme 3). Introduction of fluorine on the ring is best performed at the expense of the corresponding amino derivative, using diazotization followed by dediazonation in the presence of fluoride-containing counterion (D. E. Rosenberg and al., Tet. Let., 21, 4141-4, 1980; Scheme 3a). Other modifications of this method can also be useful (Rosenfeld and Widdowson, JCS Chem. Comm. 914, 1979). An alkyl group can be introduced by low temperature lithium halogen exchange followed by quenching with the appropriate aldehyde [see: W. E. Parham, C. K. Bradsher *Acct. Chem. Res.* 300 (1982]. The resultant alcohol can be converted to an alkyl by hydrogenolysis [*Reductions in Organic Chemistry* (M. Hudlicky, ed.), John Wiley & Sons, New York, 1984] as shown in Scheme 3. The substituents, wherein $R_1$ and $R_2$ are each independently hydroxy or alkoxy, can be introduced by low temperature lithium halogen exchange followed by quenching with the electrophilic bis(trimethylsilyl) peroxide [(TMSO)$_2$ - Scheme 3) M. Taddei and A. Ricci *Synthesis* 633–635 (1986)] which affords the silyl ether. The silyl ether can be converted to OH by treatment with hydrochloric acid [M. Taddei and A. Ricci ibid]. The alkoxy group (OR wherein R is alkyl having 1 to 6 carbon atoms) can be introduced by treating the derivative OH with weak base ($K_2CO_3$) and an appropriate alkyl halide [2 equivalents, see: C. F. H. Allen and J. W. Gates, Jr. *Organic Syntheses* Coll. Vol 3 140 (1955)] which will, in addition, form the ester. The ester can be selectively cleaved in the presence of the ether with one equivalent of sodium hydroxide (Scheme 3). The derivative where Y is carbonyl can be introduced at the benzonitrile stage using the synthetic Scheme 4a. Scheme 4b describe the conversion of the cyano group into the amidine group via the thioimidate. The thioimidate is formed by first treating the cyano compound with hydrogen sulfide ($H_2S$) followed by alkylation with methyl iodide. Next, treatment of the thioimidate with ammonium acetate affords the amidine as the salt (HI). Alternatively (Scheme 4c) the nitrile can be converted to the amidine by the use of lithium bis(trimethylsilyl)amide in an inert solvent such as diethyl ether (R. T. Boere et al, *J. Organomet. Chem.*, 331, 161-67, 1987).

Scheme 5 describes the synthesis of the lactone (3-(S)-amino-5-oxo-furane) from the corresponding protected (L)-aspartic acid (N-tBoc-aspartic acid, β-benzyl ester). First, the protected amino acid was converted to the intermediate optically active alcohol using the borane-THF reagent (C. Stanfield etal., *J. Org. Chem.* 4797-98, 46, 1981). The alcohol ester is then lactonized using acid (camphorsulphonic acid or p-toluenesulfonic acid) or basic (triethylamine) catalysis in an inert solvent such as, for example, dichloromethane. The free lactone was then obtained as its hydrochloride salt from the action of dry hydrochloric acid in a solvent such as THF or dioxane. The enantiomeric lactone can be obtained by using the same procedure in the D-amino acid series. Ring substituted lactones can be obtained by, first, converting the intermediate protected alcohol to the corresponding aldehyde using an oxidation reaction such as, the Swern reaction or pyridinium chlorochromate in an aprotic solvent such as dichloromethane or pyridine. Nucleophilic addition of a anion to the aldehyde produces the substituted alcohol which is then cyclized and deprotected as before. Substituted lactones can also be obtained by cyclization of an appropriate olefinic acid including iodolactonazation (Ansell and Palmer, *O. Rev. Chem. Soc.*, 18, 211-25, 1964).

In Scheme 6, is outlined the synthesis of bicyclic lactones. The addition of lithium amide reagents to the coumarin nucleus affords through a Michael addition the protected 4-amino-3,4-dihydro-2-oxo-2H-1-benzopyrane. Examples of lithium amide reagents that can be used in that reaction are lithium hexamethyldisilazane or lithium benzylamine. When the benzylamine used is homochiral, an entry to chiral bicyclic lactones is obtained (S. G. Davies and O. Ichihara, *Tetrahedron: Asymmetry*. 2, 183–86, 1991). The free 4-amino-3,4-dihydro-2-oxo-2H-1-benzopyrane is obtained by a suitable deprotection procedure, e.g., aqueous acid for the silyl groups and hydrogenolysis in the presence of Pd(OH)$_2$ for the benzyl group or another method as described by T. H. Greene in "*Protective Groups in Organic Synthesis*", Wiley-Interscience, 1980.

Compounds of Formula I can be obtained by coupling of one of the amino lactone derivatives obtained in Schemes 5 or 6 with the acid obtained as described in Schemes 1–4. Scheme 7 illustrates the coupling using an activated form of the acid. These activated forms include anhydrides, internal anhydride, acid chloride or one of the various activated forms as described in *Principles of Peptide Synthesis,* Bodansky, 1984, Springer-Verlag. Preferentially, the amide bonds are formed using standard coupling reagents, e.g. dicyclohexylcarbodiimide (DCC), carbonyldiimidazole, disuccinimidyl carbonate (DSC), benzotriazole-1-yl-oxy-tris-(dimethylamino)-phosphonium hexafluorophosphate (BOP) or isobutyl chloroformate (mixed anhydride method).

Scheme 8 describes an alternative synthetic route in which a protected ω-hydroxy-3-aminoacid ester, precursor to the lactone, is coupled to the 5-(benzamidine)-pentanoic acid using one of the method listed for Scheme 7. Protection of the hydroxy group is advantageously selected from tetrahydropyranyl (THP) or tert-butyldimethylsilyl (TBDMS) group introduced as described by T. H. Greene in "*Protective Groups in Organic synthesis*", Wiley-Interscience, 1980. The product resulting from this coupling is then deprotected and the lactone ring is obtained by cyclization of the hydroxy acid in acidic anhydrous conditions similar to those described in Schemes 5 and 6.

Alternatively (Scheme 9), a 5-(cyanophenyl)pentanoic acid can be used for condensation with a suitable precursor of the lactone ring, e.g., a protected hydroxy acid moiety (the most desirable ester is the t-butyl ester which can be deprotected to the acid by contact with a strong acidic medium as HBr/AcOH or trifluroacetic acid/dichloromethane). In that case, the resulting nitrile can be converted to the amidine using one of the methods outlined in Schemes 4b or 4c. The compounds of Formula I are obtained by lactonization of the intermediates (Scheme 8) using the procedures described in Scheme 4 and 5.

Purification of final compounds is usually by reverse phase high pressure liquid chromatography [*High Performance Liquid ChromatoaraDhv Protein and Peptide Chemistry,* F. Lottspeich, A. Henscher, K. P. Hupe, eds.) Walter DeGruyter, New York, 1981) or crystallization.

SCHEME 1
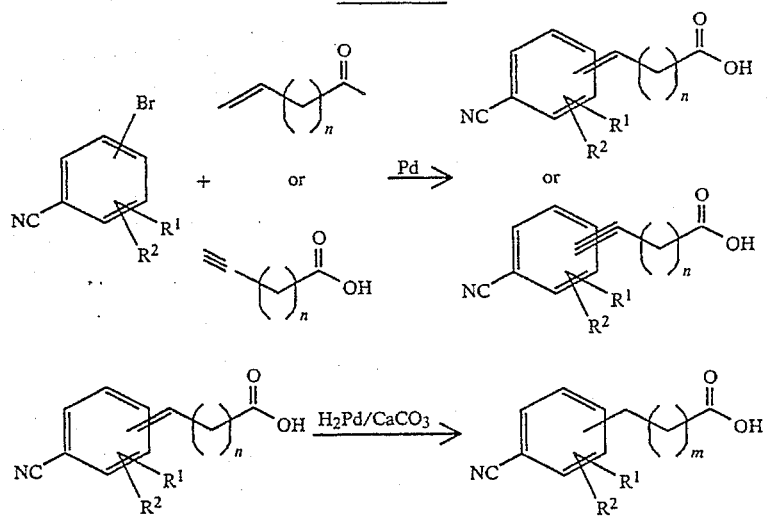
n is an integer from 1 to 3
m is an integer from 0 to 5
SCHEME 2
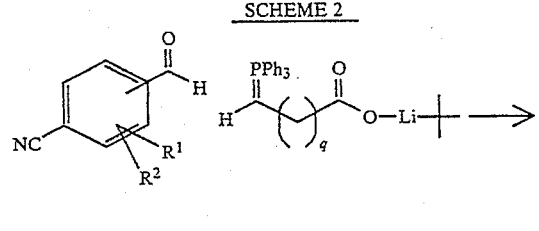
-continued SCHEME 2
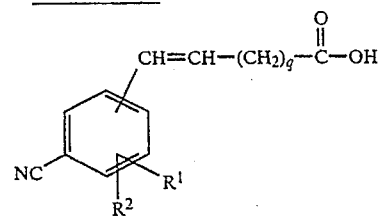
q is an integer from 1 to 4
PPh3 is triphenylphosphonium.
SCHEME 3
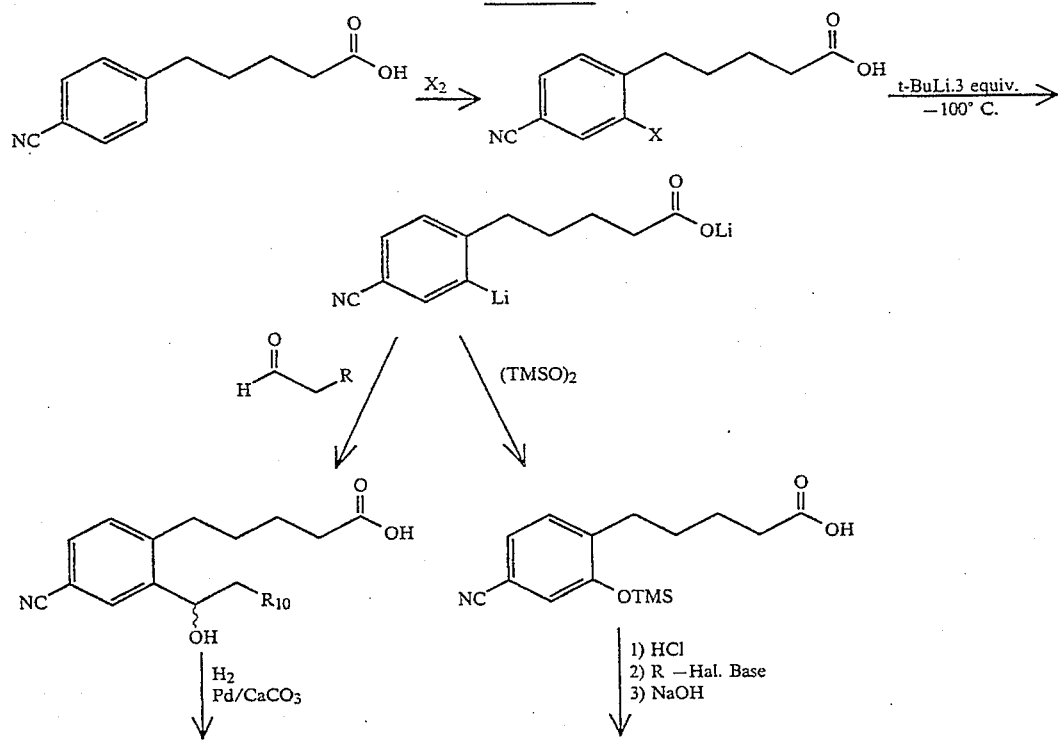

-continued
SCHEME 3
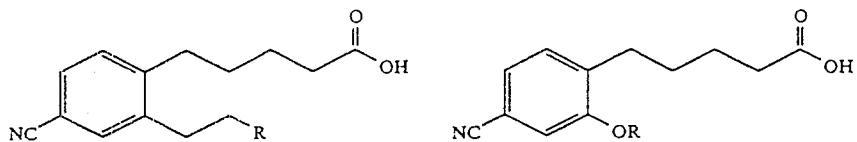
In the above scheme R is alkyl having 1 to 4 carbon atoms, $R_{10}$ is alkyl having 1 to 6 carbon atoms and $X_2$ is halo.
SCHEME 3a
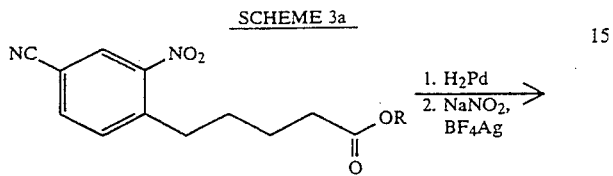
-continued
SCHEME 3a
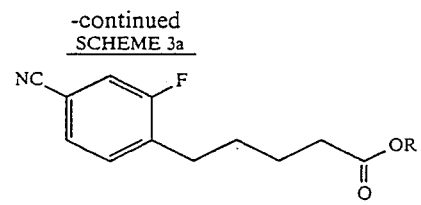
SCHEME 4
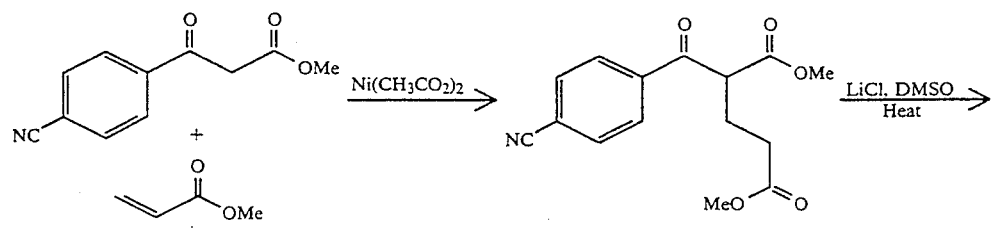
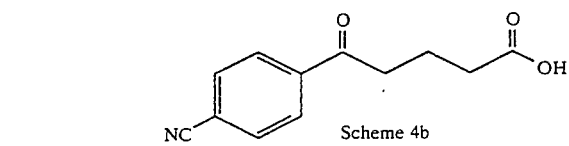
Scheme 4b
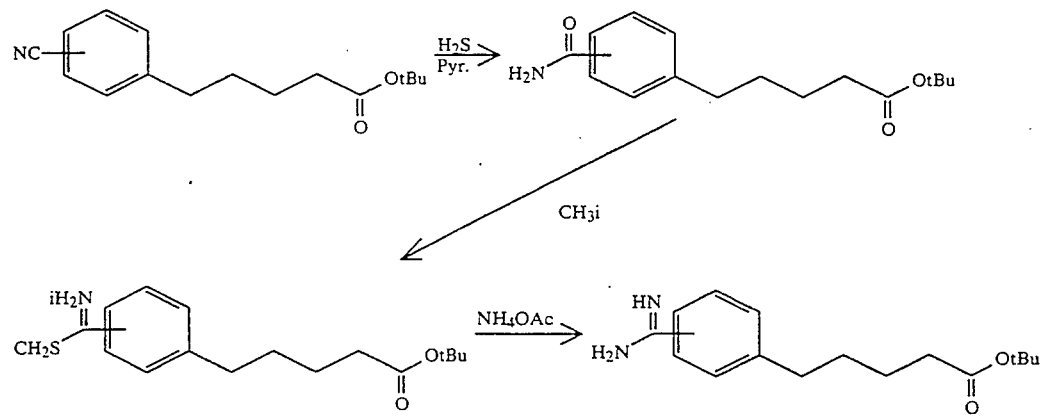
Scheme 4c
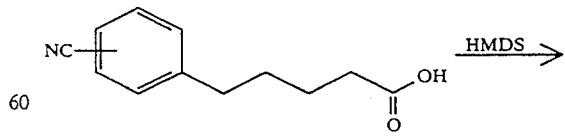

SCHEME 5
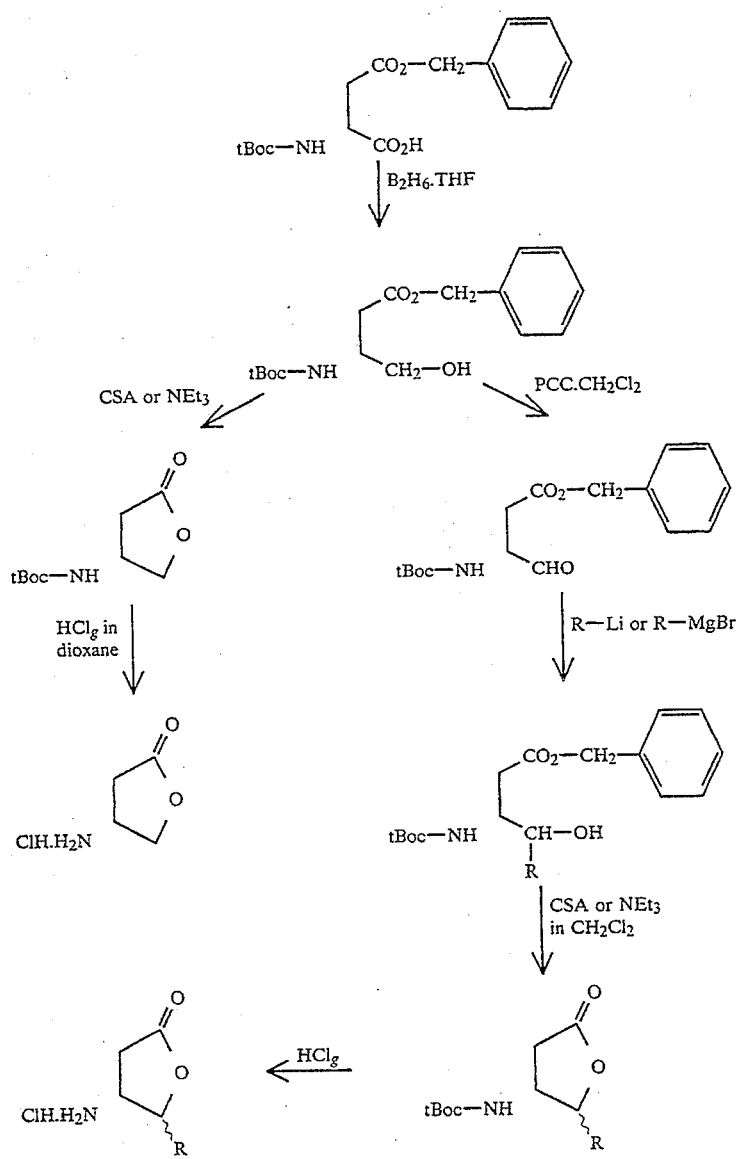
Wherein R may be alkyl, phenyl or substituted phenyl or heteroaromatic.
SCHEME 6
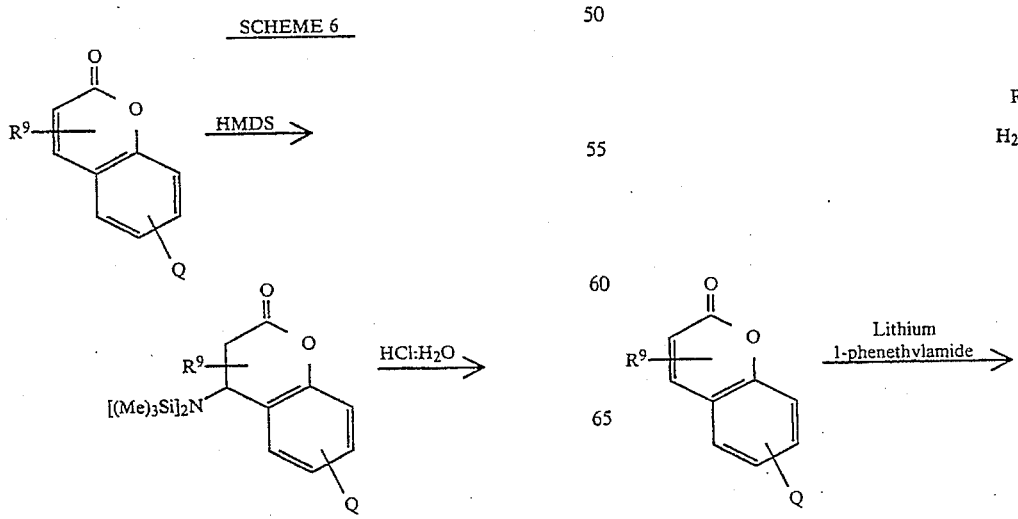
-continued
SCHEME 6
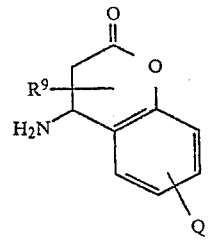

-continued
SCHEME 6

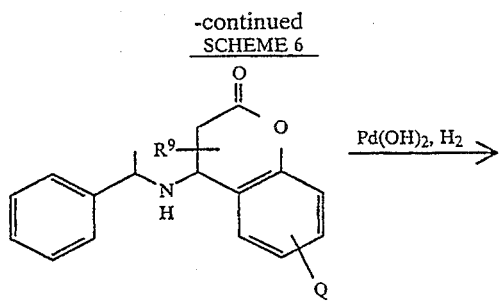

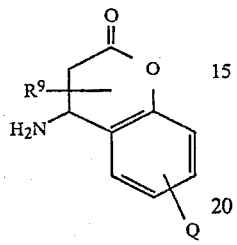

Wherein Q is defined as before.

SCHEME 7

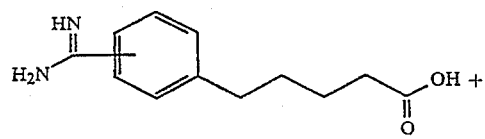

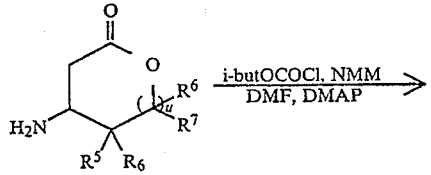

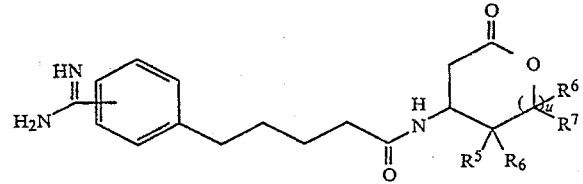

Wherein $R^5$, $R^6$, $R^7$, $R^8$ and u are defined as before.

SCHEME 8

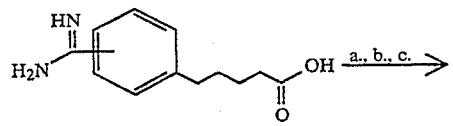

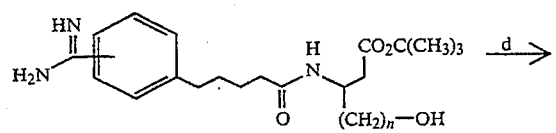

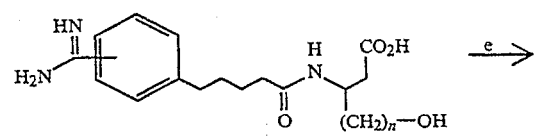

-continued
SCHEME 8

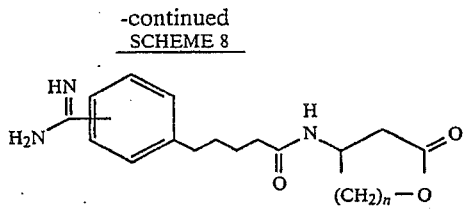

a. DMF, i-ButOCOCl, NMM. b. ω-hydroxy-3-amino acid, tbutyl ester derivative. c. NMM, DMAP. d. Aqueous TFA. e. HCl, dioxane.
Wherein n is an integer from 1 to 3.

SCHEME 9

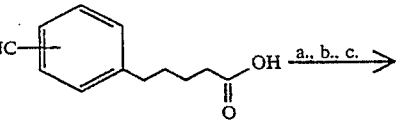

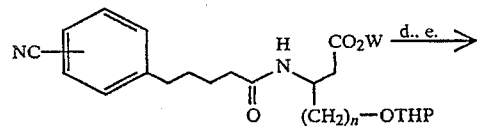

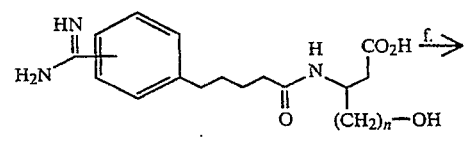

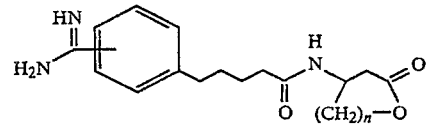

a. DMF, i-butOCOCl. b. ω-hydroxy-3-amino acid, tubtyl ester. c. NMM, DMAP. d. H2S, pyridine; MeI, acetone; NH4OAc or Hexamethyl disilazane in diethyl ether. e. Aqueous Acid. f. HCl in dioxane.
Wherien n is an integer from 1 to 3.

This invention also relates to a method of inhibiting platelet aggregation and more specifically, a method of treatment involving the administration of compounds of Formula I to achieve such inhibition.

For the inhibition of platelet aggregation, compounds of Formula I may be administered orally, parenterally, or by inhalation spray or rectally in dosage unit formulations containing conventional non-toxic pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is based on a variety of factors, including the type, age, weight, sex and medical condition of the patient; the severity of the condition; the route of administration; and the particular compound employed. Thus dosage regimen may vary widely. Dosage levels of the order from about 0.01 mg to about 150 mg per kilogram of body weight per day are useful in the treatment of the above-indicated conditions (from about 10 mg to about 150 mg per patient per day). For oral administration a daily dose of from about 0.01 to 150 mg/Kg body weight, particularly from about 1 to 30 mg/Kg body weight may be appropriate. For administration by injection a preferred daily dose would be from about 0.01 to 50 mg/Kg body weight.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may contain, for example, an amount of active ingredient from about 1 to 250 mg, preferably from about 25 to 150 mg. A suitable daily dose for a mammal may vary widely depending on the condition of the patient and other factors.

The active ingredient may also be administered by injection as a composition wherein, for example, saline, dextrose or water may be used as a suitable carrier. A suitable daily dose would typically be about 0.01 to 50 mg/kg body weight injected per day in multiple doses depending on the condition being treated.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The following Examples are intended to further illustrate the present invention and not to limit the invention in spirit or scope. In the Examples, all parts are parts by weight and temperature is in degrees Celsius unless otherwise expressly set forth.

EXAMPLE 1

Preparation of 4-(Aminoiminomethyl)-N-(5-oxo-3S-furanyl)benzenepentanamide

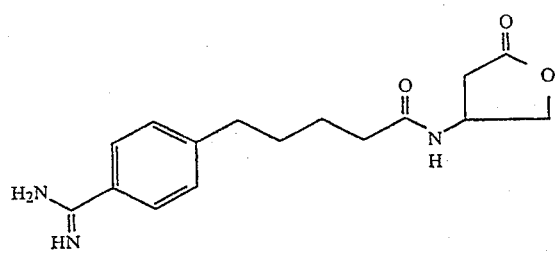

Step 1. Preparation of 3-N-tBoc-amino-4-hydroxy-(3S)-butyric acid benzyl ester

N-tBoc-L-aspartic acid, β-benzyl ester (10.0 mmol) was dissolved in 10 mL of THF and added dropwise over a period of 30 min to a 0° C. solution of $BH_3$-THF (20 mL, 20.0 mmol), under $N_2$. After the mixture was stirred for an additional 1–2 h at 0° C., the reaction was quenched with a 10 mL solution of 10% acetic acid in MeOH, and the solvent was evaporated. The residue was dissolved in EtOAc and extracted with 1N HCl 1, $H_2O$, and 1M $NH_4HCO_3$. After being dried over $MgSO_4$, the product was recovered by removal of the solvent in vacuo (mp 56°–57° C. from isopropyl ether/hexane).

Step 2. Preparation of N-tBoc-3-amino-5-oxo-3S-furane.

The 3-N-tBoc-amino-4-hydroxy-butyric acid benzyl ester (20 g, 64 mmol) was stirred in 200 mL dichloromethane at 25° C. for 16 hr in the presence of a catalytic amount of camphor sulfonic acid. Solvent was removed in vacuo. The crude material was purified by flash chromatography on a bed of silica gel (22 cm×6 cm of Merck 60 Silicagel) eluted with a gradient of hexane/ethyl acetate (90/10 to 70/30; 200 mL flow rate). The pure N-tBoc-3-amino lactone was isolated as a white solid (5.4 g).

Step 3. Preparation of 3-amino-5-oxo-3S-furane.

The 3-N-tBoc amino lactone (5.0 g, 25 mmol) isolated in Step 2 was dissolved in 20 mL 4N HCl dioxane. Gas evolution was observed. After stirring 45 min at 25° C., 10 mL of 4N HCl dioxane solution were added and after 1 hour stirring at 25° C., the excess of HCl was removed in vacuo. The resulting solution deposited crystals upon standing. The white crystalline material was filtered and dried to give 2.9 g of product; $^1H$ NMR $d_6$(DMSO) δ 2.55 (dd, 1H, $J_1=18.3$ Hz, $J_2=2.5$ Hz), 3.0 (dd, 1H, $J_1=8.5$ Hz, $J_2=18.3$ Hz), 4.1 (m, 1H), 4.35 (dd, 1H, $J_1=10.5$ Hz, $J_2=2.7$ Hz), 4.5 (dd, 1H, $J_1=10.5$ Hz, $J_2=6.5$ Hz), MS (FAB) 102.1 (MH+).

Step 4. Preparation of 5-(p-cyanophenyl)-4-pentenoic acid

Tetrabutylammonium chloride (hydrate, 17.8 g) was dried by azeotroping with benzene (250 mL round bottom flask equipped with a Dean-Stark apparatus). The benzene was removed in vacuo affording anhydrous tetrabutylammonium chloride (17.0 g, 61.2 mmol). To this flask under argon were added triphenylphosphine (820 mg, 3.13 mmol), palladium acetate (703 mg, 3.13 mmol), 4-bromobenzonitrile (16.9 g, 92.8 mmol), potassium acetate (36.8 g, 375 mmol) and 100 mL of degassed anhydrous dimethylformamide (degassed by bubbling argon through for 10 min, dried over molecular sieves). A solution of 4-pentenoic acid (6.27 g, 62.6 mmol) and-degassed anhydrous DMF (35 mL) was then added to the rapidly stirring reaction mixture at 23° C. After 21 hours at 23° C., the reaction mixture was poured slowly into a sodium carbonate solution (3%, 400 mL) and extracted with ethyl acetate (500 mL). The aqueous layer was treated with decolorizing carbon and filtered. Then, the aqueous layer was acidified to a pH of 2 with 10% HCl which afforded the title compound as a white solid (6.82 g, 54%): m.p. 150°–167° C. The above procedure affords the title compound in sufficient purity to take on to the next step without complications. An analytical sample was obtained by submitting the sample to further purification by flash chromatography (ethyl acetate:methylene chloride:acetic acid, 1:4:0.05) and recrystallization from ethyl acetate (2 times). The product was isolated as a white solid: m.p. 154°–156° C.

Elemental Analysis:

Calculated for $C_{12}H_{11}NO_2$: C, 71.63; H, 5.51; N, 6.96. Found: C, 71.50; H, 5.54; N, 6.80.

Step 5. Preparation of 5-(p-cyanophenyl)pentanoic acid

A solution of 1.47 g (7.32 mmol) of the product of Step 3 in 90 mL of methanol was hydrogenated over 200 mg of 5% Pd/CaCO3 at 5 psi hydrogen over a 1.2 h period. After removing the catalyst by filtration and evaporation of the solvent in vacuo, the residue was triturated with ether followed by hexane which afforded the title compound as a white solid. The resulting product had the following properties: m.p. 101°–102° C.

Elemental Analysis

Calculated for $C_{12}H_{13}NO_2$: C, 70.92; H, 6.45; N, 6.89. Found: C, 70.71; H, 6.56; N, 6.87.

Step 6. Preparation of 5-(p-benzamidine)-pentanoic acid

Under a nitrogen atmosphere, the reaction was carried out in a flamed dried, two neck, 500 mL round bottom flask, equipped with a magnetic stir bar. A slurry of 4.06 g (20 mmol) of 5-(p cyanophenyl)-pentanoic acid prepared in Step 4 in 60 mL of anhydrous ethyl ether was treated with 100 mL of 1M $(T_MS)_2NLi$ in hexanes by cannula and stirred overnight (20–24 hours) at 23° C. The reaction was slowly quenched with 25 mL water and the pH was adjusted to 7 using 45 mL of 20% aq. HCl. The two phase mixture was treated with 25 mL $CH_3CN$, filtered and the cake was washed with 50 mL $H_2O$; followed by 100 mL 7:3 ethyl ether:$CH_3CN$ and 50 mL ethyl ether. The cake was air dried to give 4.0 g (90%) of the 5-(p-benzamidine)-pentanoic acid as the zwitterionic compound. The zwitterionic product may be solubilized in 2N HCl. After lyophilization, the hydrochloride is isolated as an off white solid; $^1H$ NMR $d_6$(DMSO) δ 1.6 (m, 4H), 2.25 (t, 2H, J=7 Hz), 2.75 (t, 2H, J=7 Hz), 7.6 (m, 4H), 9.0 (bs, 2H), 9.25 (bs, 2H), 12.0 (s, 1H)

Step 7. Preparation of 4-(aminoiminomethyl)-N-(5-oxo-3S-furanyl)benzene pentanamide, trifluoroacetic acid salt.

4-Benzamidine pentanoic acid hydrochloride prepared in Step 6 (5 g, 18.5 mmol) was added to dry DMF (75 ml) at 0° C. followed by N-methylmorpholine (2.14 mL, 19.4 mmol) and isobutyl chloroformate (2.53 g, 18.5 mmol). The mixture was stirred for 5 min. The amino lactone as the hydrochloride salt (2.54 g, 18.5 mmol) was added followed by N-methylmorpholine (2.14 mL). After 1 h the solvent was removed under reduced pressure and the product was purified by reverse phase chromatography (water/acetonitrile) and concentrated to give 5.62 g of white solid: $^1H$ NMR $d_6$(DMSO) δ 1.6 (m, 4H), 2.06 (m, 2H), 2.3 (m, 1H), 2.7 (m, 2H), 2.85 (m, 1H), 4.05 (m, 1H), 4.45 (m, 2H), 7.6 (m, 4H), 8.4 (d, 1H, J=8 Hz), 9.0 (bs, 2H), 9.25 (bs, 2H), MS (FAB) m/e 304.0(MH+).

Step 8. Preparation of the acetate salt of 4-(aminoiminomethyl)-N-(5-oxo-3S-furanyl)benzene pentanamide The trifluoroacetic acid salt of the lactone isolated in Step 7 (2.69 g, 6.45 mmol) was mixed with 250 mL of Biorad AG1-X8 exchange resin (acetate form, 1.2 meq/mL) in 100 mL water for 60 min. The resin was filtered off, the residue concentrated, filtered through a 0.45 u pore size filter and lyophilized. Fluorine and proton NMR were consistent with complete conversion to the acetate salt. The resulting white powder had the following elemental analysis:

Elemental Analysis

Required for $C_{16}H_{21}N_3O_3 \cdot H_3C_2O_2H \cdot 0.5H_2O$ C 58.06 H 7.04 N 11.28. Found C. 57.67 H 6.77 N 11.36.

EXAMPLE 2

Preparation of (±)-4-(Aminoiminomethyl)-N-(3,4-dihydro-2-oxo-2H-1-benzopyran-4-yl) benzenepentanamide

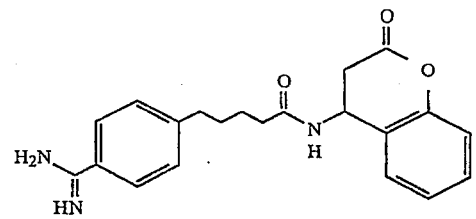

Step 1 Preparation 3-amino-3,4-dihydro-2-oxo-2H-1-benzopyrane, hydrochloride.

In a flask under nitrogen was added a solution of 10 g of coumarin in 100 mL THF to a solution of lithium bis(trimethylsilyl)amide (70 mL of a 1M solution in hexane) cooled at −78° C. The reaction mixture was allowed to warmup to 25° C. after which the solid dissolved. After complete reaction, (30 min), diethyl ether (100 mL) and water (100 mL) were added. The organic phase was decanted and dried on sodium sulfate. After removal of the solvents in vacuo, the remaining oil was dissolved in ethyl acetate and 4N HCl in dioxane (20 mL). The resulting white solid was filtered (7 g); $^1H$ NMR $d_6$(DMSO) δ 3.1 (dd, 1H, $J_1$=3.5 Hz and $J_2$=17 Hz), 3.45 (dd, 1H, $J_1$=3.5 Hz and $J_2$=17 Hz), 4.8 (m, 1H), 7.16 (d, 1H, J=8.2 Hz), 7.26 (m, 1H), 7.48 (m, 1H), 7.66 (d, 1H, J=7.5 Hz), 8.95 (bs, 3H); MS (FAB) m/e 164.3 (MH+)

Step 2. Preparation of (±)-4-(aminoiminomethyl)-N-(3,4-dihydro-2-oxo-2H-1-benzopyran-4-yl) benzenepentanamide In a flask under nitrogen atmosphere, 5-(p-benzamidine)-pentanoic acid (4 g) prepared in Step 5, Example 1 was added to dry DMF (30 ml) followed by N-methylmorpholine (1.5 g.) and isobutyl chloroformate (2 g) at 25° C. The mixture was stirred for 5 min. The 3-amino-3,4-dihydro-2-oxo-2H-1-benzopyrane (3 g) prepared in Step 1 was added followed by triethylamine (1.8 g) and a catalytic amount of 4-dimethylaminopyridine. After 1 h the solvent was removed under reduced pressure and the product was purified by reverse phase chromatography (water/acetonitrile) and lyophilized to give 3.98 g of white solid. A portion of this solid (1.5 g) was dissolved in a mixture of 20 mL of 2N HCl in dioxane and 5 mL acetonitrile and stirred overnight at 25° C. Solvent was removed in vacuo and the product was purified by reverse phase chromatography (water/acetonitrile) and lyophilized to give 1.4 g of white solid: $^1$H NMR d$_6$(DMSO) δ 1.5 (m, 4H), 2.15 (t, 2H, J=7 Hz), 2.7 (t, 2H, J=7 Hz), 2.8 (m, 1H), 3.05 (m, 1H), 5.15 (m, 1H), 7.15 (m, 2H), 7.4 (m, 4H), 7.75 (d, 2H, J=8 Hz), 8.45 (d, 1H, J=8 Hz), 9.1 (bs, 2H), 9.2 (bs, 2H); MS (FAB) m/e 366.3(MH+).

Elemental Analysis

Calculated for C$_{21}$H$_{23}$N$_3$O$_3$.F$_3$C$_2$O$_2$H.3H$_2$O: C 51.78 H 5.67 N 7.88 Found C.51.85 H 5.87 N 7.64.

EXAMPLE 3

Preparation of (±)-4-(Aminoiminomethyl)-N-(3,4-dihydro-7-methoxy-2-oxo-2H-1-benzopyran-4-yl)benzenepentanamide

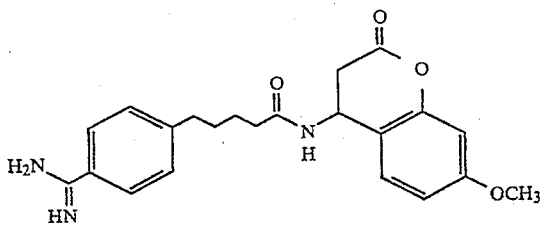

Step 1 Preparation 3-amino-3,4-dihydro-7-methoxy-2-oxo-2H-1-benzopyrane, hydrochloride.

In a flask under nitrogen was added a solution of 15 g of 7-methoxycoumarin in 100 mL THF to a solution of lithium bis(trimethylsilyl)amide (90 mL of a 1M solution in hexane) cooled at −78° C. The reaction mixture was allowed to warmup to 25° C. after which the solid dissolved. After complete reaction, (30 min), diethyl ether (100 mL) and water (100 mL) were added. The organic phase was decanted and dried on sodium sulfate. After removal of the solvents in vacuo, the remaining oil was dissolved in ethyl acetate and 4N HCl in dioxane (20 mL). The resulting white solid was filtered (6 g); $^1$H NMR d$_6$(DMSO) δ 3.1 (dd, 1H, J$_1$=4 Hz and J$_2$=17 Hz), 3.4 (dd, 1H, J$_1$=4 Hz and J$_2$=17 Hz), 3.8 (s, 3H), 4.8 (m, 1H), 6.74 (d, 1H, J=2.5 Hz), 6.8 (dd, 1H, J=2.5 Hz and 8.5 Hz), 7.53 (d, 1H, J=8.5 Hz), 9.05 (bs, 3H); MS (FAB) m/e 212 (MH+ +H$_2$O).

Step 2. Preparation of (±)-4-(aminoiminomethyl)-N-(3,4-dihydro-7-methoxy-2-oxo-2H-1-benzopyran-4-yl) benzenepentanamide In a flask under nitrogen atmosphere, 5-(p-benzamidine)-pentanoic acid (4 g) prepared in Step 5, Example 1 was added to dry DMF (30 ml) followed by N-methylmorpholine (1.5 g.) and isobutyl chloroformate (2 g) at 25° C. The mixture was stirred for 5 min. The 3-amino-3,4-dihydro-2-oxo-2H-1-benzopyrane (3 g) prepared in Step 1 was added followed by triethylamine (1.8 g) and a catalytic amount of 4-dimethylaminopyridine. After 1 h the solvent was removed under reduced pressure and the product was purified by reverse phase chromatography (water/acetonitrile) and lyophilized to give 800 mg of white solid: $^1$H NMR d$_6$(DMSO) δ 1.5 (m, 4H), 2.1 (t, 2H, J=7 Hz), 2.65 (t, 2H, J=7 Hz), 2.8 (m, 1H), 3.05 (m, 1H), 3.75 (s, 3H) 5.05 (m, 1H), 6.7 (d, 1H, J=2.5 Hz), 6.75 (dd, 1H, J$_1$=2.5 Hz, J$_2$=8 Hz), 7.2 (d, 1H, J=8 Hz), 7.4 (d, 2H, J=8 Hz), 7.75 (d, 2H, J=8 Hz), 8.45 (d, 1H, J=7.5 Hz), 9.0 (bs, 2H), 9.2 (bs, 2H); MS (FAB) m/e 396.1(MH+).

Elemental Analysis

Calculated for C$_{22}$H$_{25}$N$_3$O$_4$.F$_3$C$_2$O$_2$H.H$_2$O: C 54.65 H 5.35 N 7.97 Found C 54.4 H 5.10 N 7.78.

EXAMPLE 4

Preparation of 4-(aminoiminomethyl)-N-tetrahydro-5-oxo-2-phenyl-3S-furanyl)benzenepentanamide, trifluoroacetate (diastereoisomer A and B).

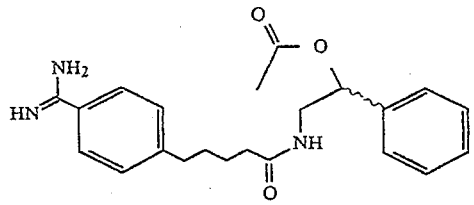

Step 1. Preparation of 3-N-tBoc-amino-4-oxo-3S-butyric acid benzyl ester.

In a flask under a static atmosphere of dry nitrogen were successively added, 12.34 g (8.48 mL) of oxalyl chloride in 50 mL dichloromethane and 10.2 g (9.19 mL) of dimethylsulfoxide in 25 mL dichloromethane. The 3-N-tBoc-amino-4-hydroxy-butyric acid benzyl ester (20 g, 65 mmol)(Example 1, Step 1) in 100 mL dichloromethane was added over 10 min. A solution of 36.24 mL of triethylamine (259 mmol, 4.0 equivalents) in 50 mL dichloromethane was slowly added over 15 min. The resulting mixture was stirred 15 min. at room temperature, quenched with 97 mL water, poured in 500 mL hexane and washed with 20% aqueous NaHSO$_4$. After work up, 19.0 g of crude aldehyde (95% yield) was obtained as a yellow viscous oil used without further purification: $^1$H NMR (CDCl$_3$) δ 1.4 (s, 9H), 3.0 (m, 2H), 4.4 (m, 1H), 5.15 (s, 2H), 5.65 (m, 1H), 7.35 (s, 5H), 9.65 (s, 1H). FAB MS: m/e 314.3 (M+Li+).

Step 2. Preparation of 3-N-tBoc-amino-4-hydroxyphenylbutyric acid benzyl ester.

A solution of the aldehyde prepared in Step 1 (1.54 g, 5 mmol) in 50 mL anhydrous diethyl ether was cooled at −45° C. in a dry ice/acetonitrile bath. Phenylmagnesium bromide (3.34 mL of a 3M solution in diethyl ether, 10 mmol) was added slowly via syringe. The reaction mixture was stirred at −45° C. for 15 min, allowed to warm up to 0° C. and poured into 250 mL 1M K$_2$HPO$_3$. Work up provided 1.91 g of a yellow viscous oil which by TLC (SiO$_2$; 7:3 hexane:ethyl acetate) showed a major spot (Rf 0.35) and a minor spot (Rf 0.67) corresponding to some residual starting material. The major spot (1.31 g), isolated by silica gel chromatography, was identified as the mixture of the two diastereoisomers of the expected product: $^1$H NMR (CDCl$_3$) δ 1.4 (m, 9H), 2.4–3.0 (m, 2H), 4.1 (m, 1H), 4.85 (m, 1H), 5.15 (m, 2H), 7.35 (m, 5H); MS (FAB) m/e 392.4(M+Li+).

Step 3. Preparation of 3-N-tBoc-amino-2-phenyl-5-oxo-3S-furane.

A solution of 5.31 g of the crude hydroxy ester prepared in Step 2 in 100 mL benzene was refluxed with a Dean-Stark trap in the presence of a catalytic amount of camphorsulphonic acid. After 6 hr reflux, the reaction was concentrated in vacuo to an oil (3.82 g): 1H NMR (300 MHz), CDCl$_3$, δ 1.35, 1.45 (s, 2:1, 9H), 2.75 (m, 2H), 4.5, 4.75 (m, 2:1, 1H), 4.7 (s, 2H), 5.1 (m, 1H), 5.7 (d, 1H), 7.35 (m, 10H); MS (FAB+) 284.6 (M+Li+).

Step 4. Preparation of 3-amino-2-phenyl-5-oxo-3S-furane, hydrochloride.

A solution of 3-N-tBoc-amino-2-phenyl-5-oxo-3S-furane (3.82 g of a mixture of diastereoisomers isolated in Step 3) in 4N HCl in dioxane was stirred for two hours. A white crystalline solid was isolated by filtration in 55% yield (1.63 g) as a 1:4 mixture of the two possible diastereoisomers: $^1$H NMR (CDCl3) δ 2.8 (m, 1H), 3.3 (m, 1H), 4.4 (m, 1H), 5.75 (d, 0.2 H, J=7 Hz), 5.85 (d, 0.8 H, J+7 Hz), 7.4 (m, 5H), 8.25 (bs, 2H); MS (FAB) m/e 178(M+H+).

Step 5. Preparation of 4-(aminoiminomethyl)-N-tetrahydro-5-oxo-2-phenyl-3S-furanyl) benzenepentanamide, trifluoroacetate (diastereomer A).

4-Benzamidine pentanoic acid (0.90 g, 3.5 mmole) prepared in Step 6 of Example 1 is added to dry DMF (20 mL) at 0° C. followed by N-methylmorpholine (0.43 mL, 3.9 mmole) and isobutyl chloroformate (0.46 mL, 3.5 mmole). The mixture is stirred for 5 min. The amino phenyl lactone as the hydrochloride salt (0.75 g, 3.5 mmole) prepared in Step 4 above is added followed by N-methylmorpholine (1 equiv.). After 16 h the solvent is removed under reduced pressure and the diasteromeric products are purified by C-18 reverse phase chromatography (water/acetonitrile) and concentrated to give a white solid after lyophilization: Diastereomer A (790 mg); $^1$H NMR (300 MHz:d$_6$-DMSO): delta; 1.1 (m, 4H), 1.7 (m, 2H), 2.4 (m, 5H), 3.1 (m, 1H), 4.8 (m, 1H), 5.6 (d, 1H), 7.2 (m, 7H), 7.7 (m, 2H), 8.05 (d, 1H), 9.1 (m, 4H); FAB MS; 380.3 (M+H) , HRMS: calc; 380.1974, obs; 380.2039.

Elemental Analysis

Calculated for $C_{22}H_{25}N_3O_3 \cdot F_3C_2O_2H \cdot H_2O$ C 56.36 H 5.51 N 8.22 Found C 55.94 H 5.30 N 8.07

EXAMPLE 5

Preparation of 4-(aminoiminomethyl)-N-(tetrahydro-5-oxo-2-phenyl-3S-furanyl)benzenepentanamide, trifluoroacetate (diastereoisomer B).

Diastereoisomer B was obtained by HPLC purification of crude reaction mixture of Example 4, Step 5 (300 mg). $^1$H NMR (300 MHz:d$_6$-DMSO): delta; 1.6 (m, 4H), 2.15 (m, 2H), 2.6 (m, 5H), 3.0 (m, 1H), 4.4 (m, 1H), 5.3 (d, 1H), 7.4 (m, 7H), 7.7 (m, 2H), 8.5 (d, 1H), 9.1 (m, 4H); FAB MS; 380.3 (M+H), HRMS: calc; 380.1974, obs; 380.2005.

Elemental Analysis

Required for $C_{22}H_{25}N_3O_3 \cdot F_3C_2O_2H \cdot 1.5H_2O$ C 55.38 H 5.61 N 8.07 Found C 55.39 H 5.19 N 7.70

EXAMPLE 6

PreparatiOn of 4-Aminoiminomethyl)-N-[2-(4-methylphenyl)-5-oxo-3S-furanyl] pentanamide, trifluoroacetic acid salt.

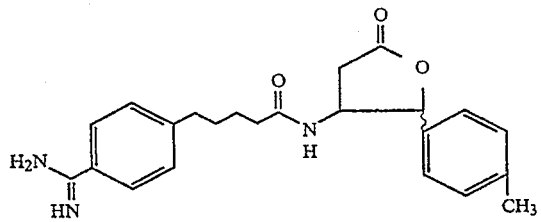

Step 1. Preparation of 3-N-tBoc-amino-4-hydroxy-(4-methylphenyl)-3S-butyric acid benzyl ester A solution of the aldehyde prepared in Step 1, Example 4, in anhydrous diethyl ether is cooled at −45° C. in a dry ice/acetonitrile bath. (4-Methylphenyl) magnesium bromide is added slowly via a syringe. The reaction mixture is stirred at −45° C. for 15 min, allowed to warm up to 0° C. and poured into 250 mL K$_2$HPO$_3$ 1M. Aqueous work up provides a yellow viscous oil. The major product is identified as the mixture of the two diastereoisomers of the expected alcohol ester.

Step 2. Preparation of 3-N-tBoc-amino-2-[4-methylphenyl]-5-oxo-3S-furane.

A solution of the crude hydroxy ester prepared in Step 2 in benzene is refluxed with a Dean-Stark trap in the presence of a catalytic amount of camphorsulphonic acid. After 6 hr reflux, the reaction is concentrated in vacuo to an oil which is used in the next step without further purification.

Step 3. Preparation of 3-amino-2(4-methylphenyl)-5-oxo-3S-furane, hydrochloride.

A solution of 3-N-tBoc-amino-2(4-methylphenyl)-5-oxo-3S-furane (a mixture of diastereoisomers isolated in Step 3) in 4N HCl in dioxane is stirred for two hours. The product as the hydrochloride salt can be obtained by filtration.

Step 4. Preparation of 4-aminoiminomethyl)-N-[2-(4-methylphenyl)-5-oxo-3S-furanyl] pentanamide, trifluoroacetic acid salt.

4-Benzamidine pentanoic acid prepared in Step 6 of Example 1 is added to dry DMF at 0° C. followed by N-methylmorpholine and isobutyl chloroformate. The mixture is stirred for 5 min. The amino lactone as the hydrochloride salt is added followed by N-methylmorpholine. After 1 h the solvent is removed under reduced pressure and the product is purified by reverse phase chromatography (water/acetonitrile) and concentrated and lyophilized to give a white solid.

EXAMPLE 7

Preparation of 4-(aminoiminomethyl)-N-[tetrahydro-5-oxo-2-(2-thiazolyl)-3S-furanyl]benzene pentanamide, bis(trifluoroacetate) (diastereoisomer A).

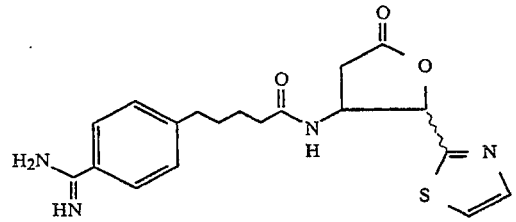

Step 1. Preparation of 3-N-tBoc-amino-4-trimethylsilyloxy-4-(thiazol-2-yl)-3S-butyric acid benzyl ester.

A solution of the aldehyde (8.6 g, 28 mmol) prepared in Step 1, Example 4, in anhydrous dichloromethane was cooled at 0°–5° C. in an ice bath. Trimethylsilyl thiazole (Fluka, 6.6 g, 42 mmol, 1.5 eq) was added dropwise via a syringe. The reaction mixture was stirred at 5° C. for 30 min, allowed to warm up to 25° C. After 1 hr stirring, the solvent was removed in vacuo to leave a light orange oil (11.7 g): $^1$H NMR (300 MHz, d$_6$-DMSO): δ, 0 (m, 6H), 0.35 (s, 3H), 1.35 (m, 9H), 2.4 (m, 2H), 4.35 (m, 1H), 5.0 (m, 3H), 7.2 (5H), 7.4 (m, 1H), 7.6 (m, 1H), 8.0 (m, 1H): MS (FAB) 471 (M+Li+).

Step 2. Preparation of 3-N-tBoc-amino-4-hydroxy-4-(thiazol-2-yl)-3S-butyric acid benzyl ester A solution of 10.7 g of the product prepared in Step 1 in 100 mL THF and 10 mL water and 2 mL of a 1.0M solution of tetrabutylammonium fluoride in THF was stirred at room temperature for 1 hr. The solvent was removed in vacuo and the resulting alcohol used in the cyclization step without further purification: MS (FAB) 399 (M+Li+)

Step 3. Preparation of 3-N-tBoc-amino-2-(thiazol-2-yl)-5-oxo-3S-furane.

A solution of 8.9 g of the product prepared in Step 2, in 200 mL benzene was refluxed with a Dean-Stark trap in the presence of a catalytic amount of camphorsulphonic acid. After 16 hr reflux, the reaction was concentrated in vacuo to an oil which was purified on a silica gel column (25% ethyl acetate in hexane containing 1% triethylamine). The lactone (1.4 g) was obtained as an oil: $^1$H NMR (DMSO-$d_6$) δ 1.5 (m, 9H), 2.65 (m, 1H), 3.1 (m, 1H), 4.3 (m, 1H), 7.4 (d, 1H, J=3.2 Hz), 7.8 (d, J=3.2 Hz); MS (FAB) 291 (M+Li+).

Step 4. Preparation of 3-amino-2-(thiazol-2-yl)-5-oxo-3S-furane, hydrochloride.

A solution of 3-N-tBoc-amino-2-(thiazol-2-yl)-5-oxo-3S-furane (isolated in Step 3) in 4N HCl in dioxane was stirred for two hours. A white crystalline solid was isolated by filtration is a mixture of two diastereoisomers: MS (FAB) 184 (MH+).

Step 5. Preparation of 4-(aminoiminomethyl)-N-[tetrahydro-5-oxo-2-(2-thiazolyl) -3S-furanyl]benzene pentanamide, bis(trifluoroacetate) (diastereoisomer A).

4-Benzamidine pentanoic acid (2.3 g, 8.9 mmole) prepared in Step 6, Example 1 was added to dry DMF at 0° C. followed by N-methylmorpholine (1.09 mL, 9.8 mmole) and isobutyl chloroformate (1.15 mL, 8.9 mmole). The mixture was stirred for 5 min. The amino thiazole lactone as the hydrochloride salt (1.90 mL, 7.4 mmole) was added followed by N-methylmorpholine. After 1 h the solvent was removed under reduced pressure. The residue was purified by reverse phase chromatography (water/acetonitrile) and appropriate fractions were concentrated to give two diastereoisomers as off-white solids: Diastereoisomer A (1.0 g, 4:1 hydroxy acid: lactone), $^1$H NMR (DMSO-$d_6$), delta, 1.5 (bm, 4H), 2.2 (m, 6H), 4.5 (m, 0.8H), 4.7 (m, 0.2H), 4.9 (d, 0.8H), 5.6 (d, 0.2H), 7.6 (m, 6.8H), 8.6 (0.2H), 9.2 (bd, 4H). MS (FAB) 387 (MH+).

Elemental Analysis:
Calculated for $C_{19}H_{24}N_4O_4S$. $F_6C_4H_2O_4$ C 44.95 H 3.94 N 9.12 Found C 44.65 H 3.99 N 9.32

EXAMPLE 8

Preparation of 4-(aminoiminomethyl)-N-[tetrahydro-5-oxo-2-(2-thiazolyl)-3S-furanyl]benzene pentanamide, trifluoroacetate. (diastereoisomer B)

Diastereomer B was obtained by HPLC separation from crude mixture Example 7 ( 2.5 g, 4:1 lactone: hydroxy acid), $^1$H NMR (DMSO-$d_6$), delta, Diastereoisomer B (2.5 g, 4:1 lactone: hydroxy acid), $^1$H NMR (DMSO$d_6$), delta, 1.55 (bm, 4H), 2.1 (m, 2H), 2.7 (m, 2H), 2.8 (dd, 2H 4.5) (m, 0.8 H), 4.7 (m, 0.2H), 7.4 (d, 2H), 7.8 (d, 2H), 7.9 (m, 2.2H), 8.6 (0.8H), 9.2 (d, 4H). MS (FAB) 387 (MH+).

Elemental Analysis:
Calculated for $C_{19}H_{22}N_4O_3S.F_4.5C_3H_{1.5}O_3$ C 47.39 H 4.25 N 10.0 C 47.34 H 4.24 N 10.1

EXAMPLE 9

Preparation of 4-(Aminoiminomethyl)-N-(4-methyl-5-oxo-3S-furanyl)-benzenepentanamide, trifluoroacetic acid salt.

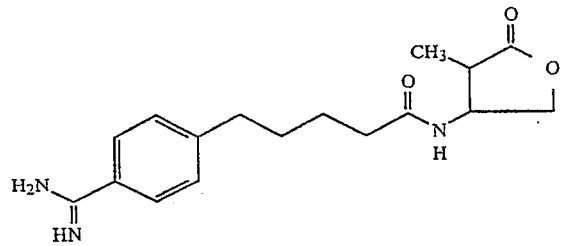

4-Benzamidine pentanoic acid prepared in Step 6, Example 1 is added to dry DMF at 0° C. followed by N-methylmorpholine and isobutyl chloroformate. The mixture is stirred for 5 min. 2-Methyl-3-amino lactone (prepared as described by K. L. Rinehart et al., J. Am. Chem. Soc., 1988, 110, 8557–58) is added followed by N-methylmorpholine. After 1 h the solvent is removed under reduced pressure and the product is purified by reverse phase chromatography (water/acetonitrile) and concentrated to give the title compound as a white solid.

EXAMPLE 10

Preparation of 4-(Aminoiminomethyl)-N-(2-vinyl-5-oxo-3S-furanyl)-benzenepentanamide, trifluoroacetic acid salt.

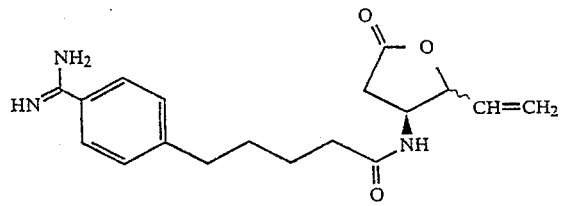

Step 1. 3-N-t-Boc-amino-4-hydroxy-(3S)-5-hexenoic acid benzyl ester.

The aldehyde (9.5 g, 31 mmole in 200 mLs diethyl ether) prepared in Example 4, Step 1 was reacted with vinyl magnesium bromide (68 mL of a 1.0M solution in tetrahydrofuran, 50 mmole) in the same manner as Example 4, Step 2 to give the desired N-protected hydroxy-ester (9.43 g golden viscous oil). The desired N-t-Boc hydroxy benzyl ester was isolated by flash chromatography using hexane: ethyl acetate. MS (FAB) 342.2 (M+Li+).

Step 2. Hydroxy - ester from Step 1 was converted to the lactone using the conditions of Example 4, Step 3. Vinyl lactone (2.3 g) contaminated with benzyl alcohol was obtained by flash chromatography (silica gel; hexane; ethyl acetate gradient). $^1$H NMR (d6-DMSO), δ, 1.40 (s, 9H), 2.6 (m, 2H), 4.2 (m, 1H), 4.4 (m, 1H), 5.2 (m, 2H) 5.8 (m, 1H). MS (FAB) 243.2 (M+Li+).

Step 3. The lactone (2.3 g) produced in Step 2 was deprotected as in Example 4, Step 4 to give the desired amine hydrochloride salt as a tan solid (hygroscopic) after trituration with diethyl ether (1.43 g). 1H NMR, d6 DMSO, δ, 3.0 (m, 2H), 4.1 (m, 1H), 4.4 (m, 1H), 5.3 (m, 2H), 6.0 (m, 1H), 8.8 (m, 3H).

Step 4. Preparation of 4-(aminoiminomethyl)-N-[2-vinyl-5-oxo-3S-furanyl]benzenepentanamide, trifluoroacetic acid salt.

4-Benzamidine pentanoic acid prepared in Step 6 of Example 1 is added to dry DMF at 0° C. followed by N-methylmorpholine and isobutyl chloroformate. The mixture is stirred for 5 min. The amino vinyl lactone as the hydrochloride salt prepared in Step 3 is added followed by N-methylmorpholine. After 1 h the solvent is removed under reduced pressure and the diastereomeric product is purified by C-18 reverse phase chromatography (water/acetonitrile), concentrated and lyophilized to give the title compound as a solid.

EXAMPLE 11

Preparation of 4-(Aminoiminomethyl)-N-(2-ethynyl-5-oxo-3S-furanyl)-benzenepentanamide, trifluoroacetic acid salt.

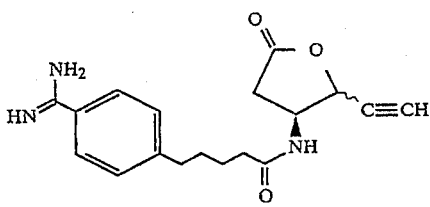

Step 1. 3-N-t-Boc-amino-4-hydroxy-(3S)-5-hexynoic acid benzyl ester.

The aldehyde prepared in Example 4, Step 1 can be reacted with ethynyl magnesium bromide in the same manner as Example 4, Step 2 to give the desired N-protected hydroxy-ester. The desired N-t-Boc hydroxy benzyl ester can be isolated by flash chromatography using hexane: ethyl acetate.

Step 2. The hydroxy - ester from Step 1 can be converted to the lactone using the conditions of Example 4, Step 3.

Step 3. The lactone produced in Step 2 can be deprotected as in Example 4, Step 4 to give the desired amine hydrochloride salt as a tan solid (hygroscopic).

Step 4. Preparation of 4-(aminoiminomethyl)-N-ethynyl-5-oxo-3S-furanyl]benzenepentanamide, trifluoroacetic acid salt.

4-Benzamidine pentanoic acid prepared in Step 6 of Example 1 is added to dry DMF at 0° C. followed by N-methylmorpholine and isobutyl chloroformate. The mixture is stirred for 5 min. The amino ethynyl lactone as the hydrochloride salt prepared in Step 3 is added followed by N-methylmorpholine. After 1 h the solvent is removed under reduced pressure and the diastereomeric product is purified by C-18 reverse phase chromatography (water/acetonitrile), concentrated and lyophilized to give the title compound as a white solid.

EXAMPLE 12

4-(Aminoiminomethyl)-N-(2-RS-bromo-5-oxo-3S-furanyl)benzenepentanamide

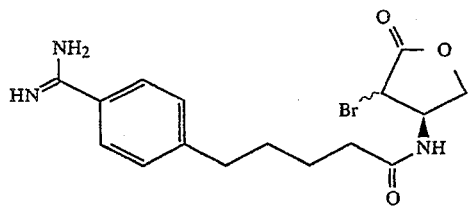

Step 1. Preparation of 2-RS-bromo-3-amino-5-oxo-3S-furane.

The 3-N-tBoc amino lactone isolated in Example 1, Step 2 can be brominated to give the desired 2-RS-bromo lactone using equimolar amounts of lactone and N-bromosuccinimide in carbon tetrachloride irradiated with a mercury lamp (Reference: J. T. Rapine, et al., J. Med. Chem., 1992, 35, 1032–1042). The desired bromolactone can be isolated by RP HPLC. The deprotected amino-2-bromo lactone can be obtained by treating the 3-N-t-Boc bromo lactone with 4N HCl dioxane. Gas evolution can be observed. At the completion of reaction excess HCl is removed in vacuo and the product isolated.

Step 2. Preparation of 4-(aminoiminomethyl)-N-[2-(RS)-bromo-5-oxo-3S-furanyl]benzenepentanamide, trifluoroacetic acid salt.

4-Benzamidine pentanoic acid prepared in Step 6 of Example 1 is added to dry DMF at 0° C. followed by N-methylmorpholine and isobutyl chloroformate. The mixture is stirred for 5 min. The 3-amino-2-bromo lactone as the hydrochloride salt prepared in Step 1 is added followed by N-methylmorpholine. After 1 h the solvent is removed under reduced pressure and the diastereomeric product is purified by C-18 reverse phase chromatography (water/acetonitrile), concentrated and lyophilized to give the title compound as a solid.

EXAMPLE 13

Compounds of the invention were evaluated by an in vivo assay to determine compound activity as an inhibitors of platelet aggregation.

In-Vitro Platelet Aggregation in PRP

Healthy male or female dogs were fasted for 8 hours prior to drawing blood; then 30 mL whole blood was collected using a butterfly needle and 30 cc plastic syringe with 3 ml of 0.129M buffered sodium citrate (3.8%). The syringe was rotated carefully as blood was drawn to mix the citrate. Platelet-rich plasma (PRP) was prepared by centrifugation at 975×g for 3.17 minutes at room temperature, allowing the centrifuge to coast to a stop without braking. The PRP was removed from the blood with a plastic pipette and placed in a plastic capped, 50 ml Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP was adjusted with PPP to a count of 2–3×10$^8$ platelets per ml. 400 μL of the PRP preparation and 50 μL of the compound to be tested or saline were preincubated for 1 minute at 37° C. in a BioData aggregometer (BioData, Horsham, Pa.). 50 μL of adenosine 5'diphosphate (ADP) (50 μm final concentration) was added to the cuvettes and the aggregation was monitored for 1 minute. All compounds are tested in duplicate. Results are calculated as follows:

Percent of control = [(maximal OD minus initial OD of compound) divided by (maximal OD minus initial OD of control saline)] × 100. The % inhibition = 100 - (percent of control).

The compounds tested and their median inhibitory concentrations ($IC_{50}$) are recorded in Table I. $IC_{50}$'s (if a compound showed 50% inhibition) were calculated by linear regression of the dose response curve. The assay results for the compounds of Examples 1, 2, 3, 4, 5, 7 and 8 are set forth in Table I, below. NT = Not Tested.

TABLE I

| Compound | Dog PRP $IC_{50}$ $1 \times 10^{-6}$ | % Inhibition | Test Concentration |
|---|---|---|---|
| 4-(Aminoiminomethyl)-N-(5-oxo-3S-furanyl)benzenepentanamide (Example 1) | — | 44 | $1 \times 10^{-5}$ |
| (±)-4-(Aminoiminomethyl)-N-(3,4-dihydro-2-oxo-2H-1-benzopyran-4-yl)benzenepentanamide (Example 2) | 2.0 | 100 | $1 \times 10^{-5}$ |
| (±)-4-(Aminoiminomethyl)-N-(3,4-dihydro-7-methoxy-2-oxo-2H-1-benzopyran-4-yl)benzenepentanamide (Example 3) | 1.1 | 96 | $1 \times 10^{-5}$ |
| 4-(aminoiminomethyl)-N-(tetrahydro-5-oxo-2-phenyl-3S-furanyl)benzenepentanamide, trifluoroacetate (diastereoisomer A) (Example 4) | 0.68 | 100 | $1 \times 10^{-5}$ |
| 4-(aminoiminomethyl)-N-(tetrahydro-5-oxo-2-phenyl-3S-furanyl)benzenepentanamide, trifluoroacetate (diastereoisomer B) (Example 5) | 5.1 | NT | NT |
| 4-(aminoiminomethyl)-N-[tetrahydro-5-oxo-2-(2-thiazolyl)-3S-furanyl]benzenepentanamide,bis(trifluoroacetate) (diastereoisomer A) (Example 7) | >10 | NT | NT |
| 4-(aminoiminomethyl)-N-[tetrahydro-5-oxo-2-(2-thiazolyl)-3S-furanyl]benzenepentanamide,bis(trifluoroacetate) (diastereoisomer B) (Example 8) | >10 | NT | NT |

What we claim is:

1. A compound of the formula

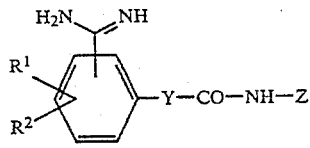

or a pharmaceutically acceptable salt thereof, wherein $R^1$ and $R^2$ are independently selected from the group consisting of hydrido, halo, alkoxy having 1 to 6 carbon atoms, alkyl having 1 to 6 carbon atoms and hydroxy;

Y is alkyl having 1 to 6 carbon atoms, alkenyl having 2 to 6 carbon atoms, alkynyl having 2 to 6 carbon atoms wherein each carbon atom of the above defined groups which is capable of further substitution may be further substituted by alkyl having 1 to 6 carbon atoms, phenyl or substituted phenyl wherein each phenyl substituent is selected from halo, alkoxy having 1 to 6 carbon atoms, and alkyl having 1 to 6 carbon atoms or Y is carbonylalkyl wherein the alkyl has 1 to 3 carbon atoms;

Z is a lactone which is represented by the formula

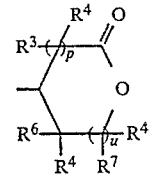

wherein $R^3$ and $R^4$ are each independently selected from the group consisting of hydrido, halo, alkoxy having 1 to 6 carbon atoms, alkyl having 1 to 6 carbon atoms and hydroxy;

$R^5$, $R^6$, $R^7$ and $R^8$ are each independently selected from the group consisting of hydrido; halo; alkenyl having 2 to 6 carbon atoms; alkynyl having 2 to 6 carbon atoms; alkoxy having 1 to 6 carbon atoms; alkyl having 1 to 6 carbon atoms; phenyl; substituted phenyl wherein each phenyl substituent is selected from halo, alkoxy having 1 to 6 carbon atoms and alkyl having 1 to 6 carbon atoms and heteroaromatic ring having 5 or 6 ring carbon atoms wherein one or two of the ring carbon atoms are replaced by a heteroatom selected from nitrogen, oxygen or sulfur with the understanding that if two hetero atoms are present one of the hetero atoms must be nitrogen;

p is an integer from 1 to 2;

u is an integer from 0 to 2;

or

Z is a lactone which is fused to a benzene ring and represented by the formula

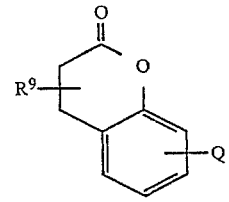

wherein Q is one or more substituents of the benzene ring which may be in any position and is selected from the group consisting of hydrido, halo, hydroxy, alkyl having 1 to 6 carbon atoms and alkoxy having 1 to 6 carbon atoms and $R^9$ is hydrido, alkyl having 1 to 6 carbon atoms or alkoxy having 1 to 6 carbon atoms.

2. A compound according to claim 1 which is 4-[aminoiminomethyl]-N-[5-oxo-3S-furanyl]benzenepentanamide.

3. A compound according to claim 1 which is 4-(aminoiminomethyl)-N-(tetrahydro-5-oxo-2-phenyl-3S-furanyl)benzenepentanamide trifluoroacetate (diastereomer A).

4. A compound according to claim 1 which is 4-(aminoiminomethyl)-N-(tetrahydro-5-oxo-2-phenyl-3S-furanyl)benzenepentanamide trifluoroacetate (diastereomer B).

5. A compound according to claim 1 which is 4-(aminoiminomethyl)-N-[tetrahydro-5-oxo-2-(2R-thiazolyl)-3S-furanyl]benzenepentanamide, bis(trifluoroacetate) (diastereomer A).

6. A compound according to claim 1 which is 4-(aminoiminomethyl)-N-[tetrahydro-5-oxo-2-(2S-thiazolyl)-3S-furanyl]benzenepentanamide, trifluoroacetate (diastereomer B).

7. A compound according to claim 1 which is (±)-4-(aminoiminomethyl)-N-(3,4-dihydro-7-methoxy-2-oxo-2H-1-benzopyran-4-yl)benzenepentanamide.

8. A compound according to claim 1 which is (±)-4-(aminoiminomethyl)-N-(3,4-dihydro-2-oxo-2H-1-benzopyran-4-yl)benzenepentanamide.

9. A pharmaceutical composition useful for inhibiting platelet aggregation comprising a therapeutically effective amount of a compound according to claim 1, together with one or more non-toxic pharmaceutically acceptable carriers.

10. A pharmaceutical composition according to claim 9 wherein the compound is selected from the group consisting of 4-[aminoiminomethyl]-N-[5-oxo-3S-furanyl]benzenepentanamide;

4-(aminoiminomethyl)-N-(tetrahydro-5-oxo-2-phenyl-3S-furanyl)benzenepentanamide, trifluoroacetate (diastereomer A);

4-(aminoiminomethyl)-N-(tetrahydro-5-oxo-2-phenyl-3S-furanyl)benzenepentanamide, trifluoroacetate (diastereomer B);

4-(aminoiminomethyl)-N-[2-(thiazol-2-yl)-5-oxo-3S-furanyl]pentanamide;

4-(aminoiminomethyl)-N-(tetrahydro-5-oxo-2-(2-thiazolyl)-3S-furanyl)benzenepentanamide, bis(trifluoroacetate) (diastereomer A);

4-(aminoiminomethyl)-N-(tetrahydro-5-oxo-2-(2-thiazolyl)-3S-furanyl)benzenepentanamide, trifluoroacetate (diastereomer B);

(±)-4-(aminoiminomethyl)-N-(3,4-dihydro-7-methoxy-2-oxo-2H-1-benzopyran-4-yl) benzenepentanamide;

and (±)-4-(aminoiminomethyl)-N-(3,4-dihydro-2-oxo-2H-1-benzopyran-4-yl)benzenepentanamide.

11. A method of treating a mammal to inhibit platelet aggregation comprising administering a theraupeutically effective dose of a compound according to claim 1 to a mammal in need of such treatment.

12. A method according to claim 11 wherein the compound is selected from the group consisting of 4-[aminoiminomethyl]-N-[5-oxo-3S-furanyl]benzenepentanamide;

4-(aminoiminomethyl)-N-(tetrahydro-5-oxo-2-phenyl-3S-furanyl)benzenepentanamide, trifluoroacetate (diastereomer A);

4-(aminoiminomethyl)-N-(tetrahydro-5-oxo-2-phenyl-3S-furanyl)benzenepentanamide, trifluoroacetate (diastereomer B);

4-(aminoiminomethyl)-N-[2-(thiazol-2-yl)-5-oxo-3S-furanyl]pentanamide;

4-(aminoiminomethyl)-N-(tetrahydro-5-oxo-2-(2-thiazolyl)-3S-furanyl)benzenepentanamide, bis(trifluoroacetate) Diastereomer A);

4-(aminoiminomethyl)-N-(tetrahydro-5-oxo-2-(2-thiazolyl)-3S-furanyl)benzenepentanamide, trifluoroacetate (diastereomer B);

(±)-4-(aminoiminomethyl)-N-(3,4-dihydro-7-methoxy-2-oxo-2H-1-benzopyran-4-yl) benzenepentanamide;

and (±)-4-(aminoiminomethyl)-N-(3,4-dihydro-2-oxo-2H-1-benzopyran-4-yl)benzenepentanamide.

* * * * *